United States Patent [19]
Odaka et al.

[11] Patent Number: 5,553,115
[45] Date of Patent: Sep. 3, 1996

[54] MEDICAL X-RAY APPARATUS, IRRADIATION TUBE, MEDICAL POSITION INDICATING APPARATUS, AND LIGHT SOURCE CONTROL CIRCUIT FOR USE IN COMBINATION WITH THE FOREGOING APPARATUSES

[75] Inventors: Masaki Odaka; Eiichi Arai; Yoshihide Okagami; Akira Yuba, all of Kyoto, Japan

[73] Assignee: J. Morita Manufacturing Corporation, Kyoto, Japan

[21] Appl. No.: 255,477

[22] Filed: Jun. 8, 1994

[30] Foreign Application Priority Data

Jun. 16, 1993 [JP] Japan .................. 5-032427 U
Sep. 30, 1993 [JP] Japan .................. 5-053231 U
Mar. 7, 1994 [JP] Japan .................. 6-036090

[51] Int. Cl.$^6$ .................................. A61B 6/14
[52] U.S. Cl. ................ 378/206; 378/170; 378/205
[58] Field of Search .......................... 378/204, 205, 378/206, 168, 170, 195, 177, 208, 95, 117

[56] References Cited

U.S. PATENT DOCUMENTS

| | | | |
|---|---|---|---|
| 1,378,007 | 5/1921 | Campion | 378/195 |
| 1,753,151 | 4/1930 | Israel | 378/170 X |
| 2,939,008 | 5/1960 | Goodfriend | 378/170 X |
| 3,745,344 | 7/1973 | Updegrave | 378/178 |
| 3,777,140 | 12/1973 | Graf | 378/170 |
| 4,426,726 | 1/1984 | Cheetham | 378/206 |
| 5,068,887 | 11/1991 | Hughes | 378/206 |

FOREIGN PATENT DOCUMENTS

| | | |
|---|---|---|
| 1021814 | 2/1953 | France. |
| 2648561 | 12/1990 | France. |
| 55-51280 | 4/1980 | Japan. |
| 57-109811 | 7/1982 | Japan. |
| 58-1405 | 1/1983 | Japan. |
| 55-166213 | 11/1988 | Japan. |

OTHER PUBLICATIONS

Title: "Sieman's Optical Viewfinder for the X–ray Machine" Author: Unknown Date of Publication: Unknown (Assumedly in 1955) Place of Publication: Germany.

*Primary Examiner*—David P. Porta
*Attorney, Agent, or Firm*—Koda and Androlia

[57] ABSTRACT

A medical X-ray apparatus capable of indicating the center of radiation cone of X-ray, regardless of the positioning distance or angle, always with high visibility on the irradiation surface of the patient, in which a plurality of visible optical means are provided outside the radiation cone of X-ray at intervals in the peripheral direction of an irradiation tube, and the visible optical means generates a visible light on a plane including the axis of X-ray, and thereby emitting a cross optical pattern on the irradiation surface of the patient, and the center of X-ray irradiation can be indicated on the irradiation surface as the intersecting position of the linear optical images. An X-ray irradiation tube which can be incorporated in the X-ray apparatus, and which is excellent in controllability, small in power consumption, capable of obtaining a stable quantity of light, and light in weight and small in size is also provided.

4 Claims, 23 Drawing Sheets

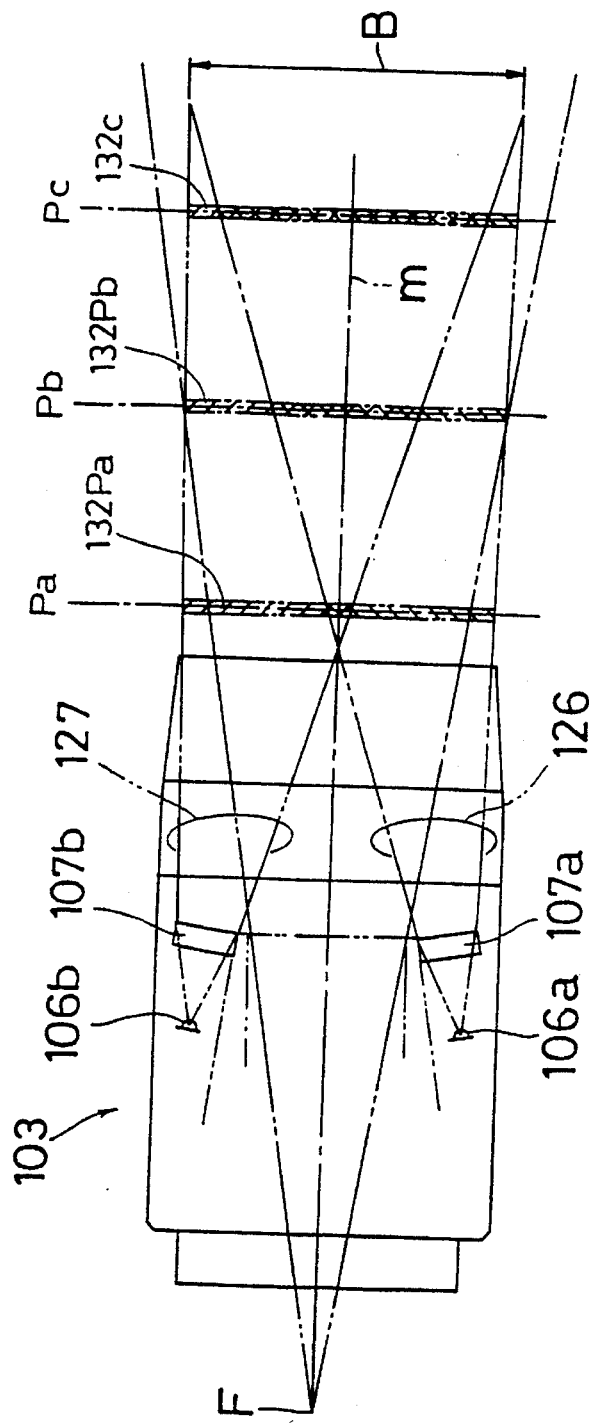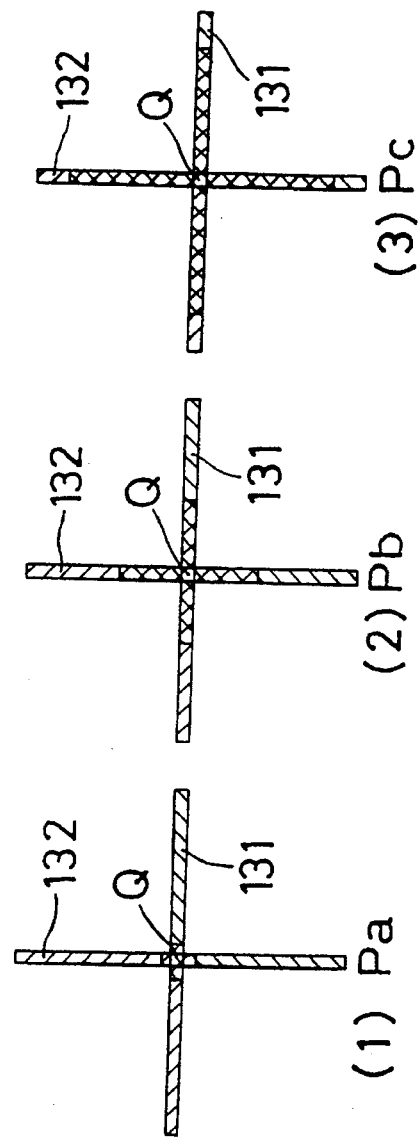
Fig.17a
Fig.17b

MEDICAL X-RAY APPARATUS, IRRADIATION TUBE, MEDICAL POSITION INDICATING APPARATUS, AND LIGHT SOURCE CONTROL CIRCUIT FOR USE IN COMBINATION WITH THE FOREGOING APPARATUSES

BACKGROUND OF THE INVENTION

1. Field of the Invention

The present invention relates to a medical X-ray apparatus and an irradiation tube. In particular, it relates to a dental X-ray apparatus such as oral radiographic X-ray apparatus as well as to an irradiation tube for use in the dental X-ray apparatus. In addition, the invention relates to a light source control circuit for lighting a light source for a specific period of time which can be incorporated in the medical X-ray apparatus and the irradiation tube.

The invention further relates to a medical position indicating apparatus for indicating an irradiating position of invisible electromagnetic waves such as X-ray, infrared ray and ultraviolet ray used in the medical care field.

2. Description of the Related Art

The dental X-ray apparatus for oral radiography is the only radiographic apparatus legally permitted to emit X-ray to a radiographic film being inserted into the oral cavity in a region of a subject larger than the size thereof. For an ordinary film size of 30×40 mm (film diagonal size 50 mm), in various standards irradiation exceeding the film diagonal size at the end portion of an irradiation tube is permitted in the oral radiography. However, such irradiation is not allowed in other radiographic applications.

This is because, in the dental X-ray apparatus for oral radiography, unlike other radiographic apparatuses, the apparatus and film are not always used at a specific dimension, but the angle and distance vary with the desired radiographic position, and moreover, since the film is put into the mouth of a patient, the film position cannot be directly observed by a radiologist. Also, a radiation cone of X-ray, that is, a radiation field does not fit within the film, and it often causes a radiographic error referred to as "cone-cut." When a cone-cut occurs, it is necessary to take an X-ray again, which leads to increased exposure dose of the patient. To reduce this risk, it is advisable to emit an X-ray in a wider area exceeding the film size. Thus, in the dental X-ray apparatus for oral radiography, even if the exposure area is determined to be slightly greater than the film size, the total exposure dose of the patient can be reduced as compared with multiple exposures of X-ray.

However, even in such dental X-ray apparatus permitted to emit X-ray in a region exceeding the film size, it is desired that the number of exposures be decreased, and the exposure dose and exposure area also be reduced, from the viewpoint of reduction of the exposure dose of the patient. It is necessary, for this purpose, to improve the positioning performance and positioning reproducibility of the X-ray apparatus. As used herein, "the positioning reproducibility" refers not only to the positioning reproducibility of X-ray irradiation field, but also to the positioning reproducibility of an irradiation angle. Such reproducibility is important in comparing observations before and after the operation or the treatment of a patient. In the prior art, a dental X-ray apparatus includes the indications of graduations so that the irradiation angle of the apparatus can be determined by a radiologist. This, however, does not sufficiently improve the reproducibility. To enhance the reproducibility, attempts have been made to optically determine a position with visible light.

Typical prior art is disclosed in the Japanese Unexamined Utility Model Publication (KOKAI) No. JP-U 55-51280 (1980). In this prior art, a visible optical system for displaying a visible spot light in the X-ray irradiation position of a subject is constructed so as to move freely in and out between a position coaxial with the X-ray irradiation axis of a irradiation tube, and a retracted position outside the irradiation region.

However, since the visible optical system is moved mechanically, the position of the visible spot light may vary every time because of dimensional errors or assembly errors of the moving and stopping mechanism. The reproducibility is thus expected to be poor. Also, in observing the visible spot light, it is hard to pin-point the position and direction of the X-ray irradiation field.

Further, after positioning with spot light, it is necessary to put aside the visible optical system mechanically to the retracted position, and therefore, the positioning once set may be deviated by the retracting action.

In this prior art, the position of focusing the spot light, that is, the position where the diameter of the spot light is the minimum, is a certain point in the optical axis direction, and the diameter of the spot light greater in the front and rear of the focus point than that at the focus point. When positioned by emitting spot light to the subject at a relatively shallow angle, that is, when emitting spot light obliquely, not from the front of the subject, the emitted spot light may be elliptical, or the spot light shape may be distorted by the body of the subject, such as a facial shape or skin asperities. It will be then difficult to accurately determine an optical axis, that is, the axis of X-ray.

Another prior art is Japanese Unexamined Utility Model Publication (KOKAI) No. JP-U 55-166213 (1980). This prior art reference discloses an optical conductor body in a tubular shape which approximates a radiation cone of X-ray. It is designed to emit light so as to draw a contour of the X-ray irradiation field with visible light ray. However, since the contour shape of sighting beam is a ring form, it is difficult to clearly judge the center of the X-ray irradiation field.

A further prior art reference is Japanese Unexamined Utility Model Publication (KOKAI) No. JP-U 58-1405 (1983), in which spot light is emitted to a certain point on the axis of X-ray from three positions provided at intervals in the circumferential direction of the irradiation tube. In this prior art, a plurality of irradiation spot lights appear in the front and the back of the focus point on the axis of the X-ray. Therefore, in this prior art, it will also be difficult to judge the center of irradiation field.

In a conventional X-ray irradiation tube, to illuminate a light source for generating a sighting beam, a power switch attached to the irradiation tube or X-ray apparatus must be manipulated. Types of power switch include: 1) an automatic reset switch which closes contact when the switch is pressed and which opens contact when released; and 2) a toggle switch which keeps contact closed or open by the latch mechanism of lever and the like. When the automatic reset type switch (1) is used as a power switch, the irradiation tube must be positioned while pressing the switch, and the operation is thus complicated and the controllability is poor. In the toggle switch (2), once the switch is on, the positioning operation can be done without any further action. However, when the switch is turned off after positioning, an extra force may prevail and the position may be deviated. Power may be wasted if the switch is forgotten to be turned off.

To have the X-ray irradiation tube to be detachable from any desired type of X-ray apparatus, a battery or power supply unit must be built in the irradiation tube itself. In the X-ray apparatus, a light source starting circuit of power-saving type is indispensable to increasing the number of exposures of the sighting beam. In this case, if output voltage is lowered gradually due to discharge characteristics of the battery, the light source exposure quantity fluctuates and the illumination of the sighting beam varies. Thus, the controllability is impaired. To replace for an X-ray irradiation tube without a boresight mechanism, a small and lightweight X-ray irradiation tube is required.

SUMMARY OF THE INVENTION

It is a primary object of the invention to provide a medical X-ray apparatus, an irradiation tube, and a medical position indicating apparatus which are capable of accurately locating the center of irradiation field in the positioning of irradiation of invisible electromagnetic waves such as X-ray, infrared ray and ultraviolet ray.

It is another object of the invention to provide a light source control circuit for a small and lightweight X-ray irradiation tube which possesses excellent controllability, consumes small power, and which is capable of generating a stable quantity of light, as well as to provide an irradiation tube and a medical X-ray apparatus which incorporate such circuit.

According to the invention, there is provided a medical X-ray apparatus comprising:

an X-ray generating unit;

an irradiation tube mounted on the X-ray generating unit to define an X-ray radiation cone from the X-ray generating unit, the irradiation tube having, outside the radiation cone, a plurality of visible optical means disposed at intervals in the peripheral direction of the irradiation tube, the visible optical means generating visible light in a plane form including the axis of the X-ray.

According to the invention, there is also provided a medical X-ray apparatus, comprising:

an X-ray generating unit;

an irradiation tube mounted on the X-ray generating unit to define an X-ray radiation cone from the X-ray generating unit, the irradiation tube having visible optical means for emitting visible light to an X-ray exposure subject to indicate an X-ray irradiation position on the X-ray exposure subject, and at least one of the irradiation tube and the X-ray generation unit having a flat switch disposed on the outer circumference thereof for controlling on/off of the visible optical means.

In one aspect of the invention, the X-ray generation unit is mounted on an arm so as to freely, angularily displace around the rotational axis that intersects the axis of the X-ray, and the flat switch is disposed on either side or both sides of the rotational axis in the axial direction of the X-ray.

In another aspect of the invention, at least a tip of the irradiation tube is formed of a light-permeable material.

In a further aspect of the invention, a tip of the irradiation tube is detachable from the irradiation tube.

In a still further aspect of the invention, the irradiation tube is mounted on the X-ray generation unit so as to freely, angularily displace around the axis of the X-ray with respect to the X-ray generating unit.

According to the invention, there is provided an irradiation tube comprising:

a tube body for guiding an X-ray radiation cone; and a plurality of visible optical means disposed on the tube body, outside the radiation cone, at intervals in the peripheral direction of the irradiation tube, the visible optical means generating visible light in a plane form including the axis of the X-ray.

According to the invention, there is provided an irradiation tube comprising:

a tube body for guiding an X-ray radiation cone;

visible optical means for emitting visible light to an X-ray exposure subject to indicate an X-ray irradiation position on the X-ray exposure subject, the visible optical means being disposed on the tube body; and a flat switch for controlling on/off of the visible optical means, the flat switch being disposed on the outer circumference of the tube body.

In one aspect of the invention, the tube body has a battery built therein for feeding electric power to the visible optical means.

According to the invention, there is provided an irradiation tube comprising:

a tube body for guiding an X-ray radiation cone, the tube body including a base end, a tip of the base end facing an exposure subject;

a tube tip portion detachably mounted on the tube body at the base end; and a support piece fixed on the tube body, the support piece projecting forward from the base end and supporting the tube tip portion at the tip of the base end, wherein the length of the support piece being projected is selected to be a value that insures a permissible distance SSD between a focus of the X-ray and an irradiation surface of the exposure subject.

According to the invention, there is provided a medical position indicating apparatus comprising:

a tube body having a hollow part for passing an invisible electromagnetic wave;

a plurality of visible optical means disposed on the tube body at intervals in the circumferential direction thereof, the visible optical means externally surrounding the hollow part of the tube body and generating a visible light in a plane form that includes the axis of the invisible electromagnetic wave.

In one aspect of the invention, the visible optical means is provided with a light source for generating a visible light and a lens for focusing the visible light from the light source into a plane form.

In another aspect of the invention, the visible light in a plane form intersects the axis of the invisible electromagnetic wave.

In a further aspect of the invention, the visible light in a plane form orthogonally crosses the axis of the invisible electromagnetic wave.

In a still further aspect of the invention, an operation switch for on/off control of the light source is provided on the outer circumference of the tube body, and when the operation switch is turned on, the light source is lit up for a predetermined period.

In a still further aspect of the invention, the light source is a light-emitting diode.

According to the invention, there is provided a light source control circuit for use in combination with a medical X-ray apparatus comprising:

a timer circuit for generating pulses of a predetermined time width after start of energization; and a switching circuit for energizing the light source while the timer circuit is generating pulses, the switching circuit discontinuing energization of the light source and the timer circuit when the pulse output of the timer circuit is over.

According to the invention, there is also provided light source control circuit for use in combination with medical X-ray apparatus comprising:

a timer circuit for generating pulses of a predetermined time width after start of energization;

a switching element for controlling the energization of light source and the timer circuit simultaneously;

a start circuit for actuating the switching element; and a conduction holding circuit for maintaining conduction of the switching element while the timer circuit is generating pulses, and for cutting off the switching element when the pulse output of the timer circuit is over.

According to the invention, there is provided a light source control circuit for use in combination with a medical X-ray apparatus comprising:

a timer circuit for generating pulses of a predetermined time width after start of energization;

a first switching element for controlling the energization of a light source and the timer circuit simultaneously;

a start circuit for actuating the first switching element; and a second switching element for allowing energization of the light source while the timer circuit is generating pulses, wherein the first switching element maintains a conduction state thereof while current is flowing into the light source, and is made a cut-off state while no current is flowing into the light source.

In one aspect of the invention, the first switching element is a thyristor.

In another aspect of the invention, the starting circuit is an automatic reset switch.

In a further aspect of the invention, the power source is a battery.

In a still further aspect of the invention, a constant current circuit for accuating the light source with a constant current is provided.

In an still further aspect of the invention, the light source is a light-emitting diode.

According to the invention, there is provided an irradiation tube comprising:

a tube body for guiding an X-ray radiation cone;

a plurality of light sources disposed, outside the radiation cone and inside the tube body, at intervals in the peripheral direction of the tube body; and a light source control circuit comprising a timer circuit for generating pulses of predetermined time width after start of energization; and a switching circuit for energizing the light source while the timer circuit is generating pulses, the switching circuit discontinuing energization of the light source and the timer circuit when the pulse output of the timer circuit is over.

In one aspect of the invention, four light sources are symmetrically disposed on the tube body as seen from the axial direction thereof and focusing means for focusing the light from each light source in a linear form to form a cross slit image on the focusing plane is provided in the tube body.

According to the invention, there is provided a medical X-ray apparatus comprising:

an X-ray generating means for generating an X-ray;

an irradiation tube detachably mounted on the X-ray generating means, the irradiation tube emitting a ray of light in a plane form including the axis of the X-ray;

an X-ray control means for controlling the X-ray generating means; and a power source means for feeding electric power to the X-ray control means, the power source means supplying the irradiation tube with electric power.

BRIEF DESCRIPTION OF THE DRAWINGS

Other and further objects, features, and advantages of the invention will be more explicit from the following detailed description taken with reference to the drawings wherein:

FIG. 17(a) is a simplified view showing cylindrical lenses seen from cut-off section line A—A in FIG. 1, and FIG. 17(b) represents beams focused by the respective lenses;

DETAILED DESCRIPTION OF THE INVENTION

Figure 1:
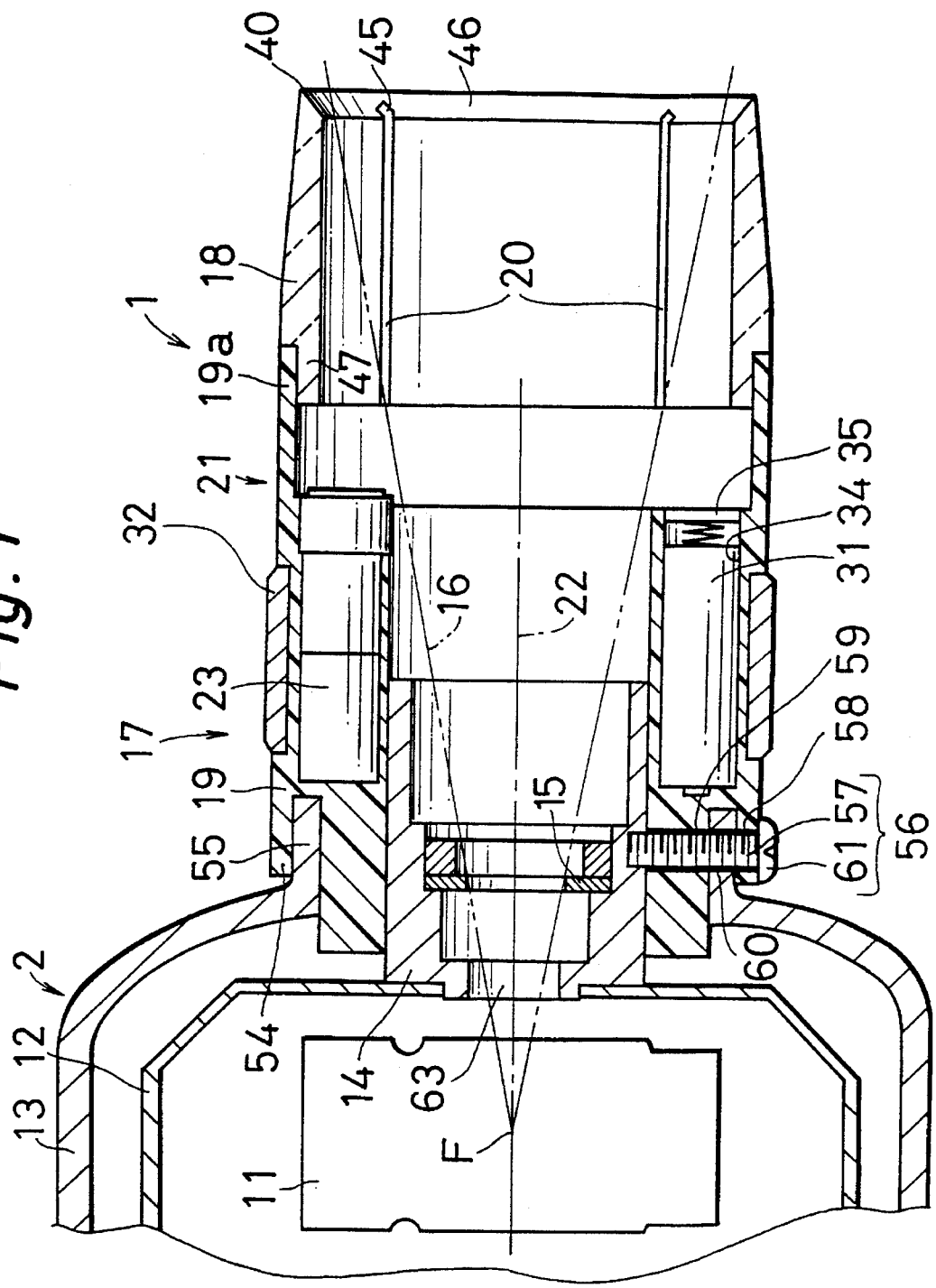
FIG. 1 is a sectional view showing a part of an X-ray apparatus and an irradiation tube 1 embodied in the invention.

According to the invention, a plurality of visible optical means are disposed on an irradiation tube outside an X-ray radiation cone, preferably at intervals in the peripheral direction of the tube. These visible optical means generate visible lights in a plane form, including the axis of X-ray. Therefore, the visible lights in a plane form from the plural visible optical means intersect linearly on the axis of X-ray. The optical pattern illuminated on a plane to be irradiated is, for example, a cross form. Regardless of the distance to the surface of an exposure subject in the axial direction of X-ray, the intersection of the visible lights is accurately displayed on the surface of the exposure subject. Such is the case regardless of the X-ray irradiation angle to the exposure subject, where the subject has irregular asperities. If, for example, the intersection of visible lights is not located on the skin, the position of intersection can be easily estimated by rotating the sector beam of the visible light about the axis of X-ray.

Thus, according to the invention the axis of X-ray can always be displayed with high visibility, regardless of the positioning distance and angle. As a result, the positioning performance may be enhanced dramatically. Also, the invention prevents radiographic positioning errors from causing the cone cut, which is a deviation of a film or X-ray detection sensor from the irradiation field arising from a radiation cone of X-ray. This reduces the risk of retaking of X-ray, and moreover the positioning precision can be enhanced. The irradiation cone of X-ray can be narrowed and the exposure dose of a patient can be decreased notably by decreasing the irradiation field.

In the invention, the switch for on/off control of each visible optical means is formed of a flat switch. This flat switch is formed in a wide area on the outer circumference of at least one of the irradiation tube and the X-ray generation unit, including a portion thereof normally touched by the radiologist. The flat switch can be manipulated easily when the radiologist operates the irradiation tube and X-ray generation unit by holding them in hand in the positioning work. Thus, it is possible for the radiologist to work without minding the visible ray lighting/extinguishing operations.

The visible optical means can easily be turned on and off. Depending on the radiographic position, a fan-shaped visible light beam crosses the eye of the patient. In such a case, the radiologist can light the visible optical means only for a minimum required time when positioning, and can extinguish it after positioning until X-ray radiography has been completed. Thus, the pain of the patient due to glare can be alleviated. In particular, if the patient is hypersensitive to light, the patient moves the body when visible light beam gets in the eyes during radiography. As a result, the positioning once determined may be deviated, and it is likely to cause blurring in the image produced. This problem is solved in the invention.

In the invention, the X-ray generation unit is mounted on an arm so as to be displaced angularly about a rotational axis such as a horizontal axis. The flat switch is disposed at one or both sides in the axis direction of X-ray about the rotational axis. When positioning by displacing angularly about the rotational axis of the X-ray generation unit, the radiologist can easily effect the on/off control of the visible optical means by touching the X-ray generation unit or irradiation tube. Thus, the controllability is enhanced.

The rotational axis may be one that intersects the axial direction of X-ray, for example, a horizontal axis.

According to the invention, at least a tip of the irradiation tube is made of a light permeable material. With the front end of the tip being as close as possible to the exposure side of the patient, the intersecting point of the optical pattern that indicates the axis of an X-ray radiation cone, for example, a cross optical image can be observed closely, thereby making it possible to limit the exposure region and to position more accurately. On the other hand, in the case of a light-shielding tip, even if the visible light pattern indicating the axis of the radiation cone of X-ray is emitted, the visible light pattern can be observed only from a very shallow angle with respect to the exposure side when the front end of the tip is brought closer to the exposure side of the patient. As a result, it would become very difficult to recognize a crossed optical pattern, that is, the central indication point of the X-ray radiation cone. In order to clearly recognize the center of the X-ray radiation cone by the visible light pattern from the observation at a shallow angle to the axis of the X-ray radiation cone i.e. from the position close to the axis, it would be required to extend the distance between the front end of the tip and the exposure surface of the patient. Thereby, the X-ray spreads conically from the focus of the X-ray tube, and the exposure region of the patient becomes larger. This brings about diminished X-ray dose on the X-ray receiving plane such as a film and an X-ray detection sensor, which makes it necessary to prolong the exposure time. Thus, the total exposure dose of the patient increases. In the invention, such problem can be solved by employing the irradiation tube at least the tip of which is made of a light-permeable material.

Moreover, according to the invention, the tip of the irradiation tube is detachable, and the tip can be changed for every patient, so that risk of infection by virus within a hospital can be prevented. The tip may be made of either a material that can be sterilized repeatedly, or made of a disposable material.

In the invention, an X-ray limiting diaphragm made of a material capable of shielding or attenuating X-ray such as lead and antimony is incorporated in the detachable tip. Thus, the exposure dose of the patient can be reduced. By replacing the X-ray diaphragm, the exposure dose can further be reduced since the X-ray can be emitted in a minimum irradiation field depending on the film size to be used.

Further in the invention, the irradiation tube is installed in the X-ray generation unit so as to be displaceable angularly about the axis. The intersecting visible light pattern of a flat sector beam indicating the axis of the radiation cone of X-ray, that is, the center of the irradiation field can be displaced angularly while keeping the state of the intersecting point of the visible light matched with the axis of the X-ray radiation cone, depending on the angular displacement of the irradiation tube. In an actual clinical operation, the radiologist can match the linear optical pattern formed by the flat sector beam of visible light with a radiographic reference line that is most suited to the radiographic position. The image reproducibility can thus be improved outstandingly. The radiographic reference line is, for example, a dental axis or a plane of occlusion, both of which could be anatomically significant, or a line linking two arbitrary points on the face determined by the radiologist to obtain reproducibility for later radiography, or eye-ear horizontal line or nasal audible lead. If, the patient is hypersensitive to light, the visible light pattern can be offset from the eyes of the patient by angular displacement of the irradiation tube, so that the pain of the patient can be alleviated.

In the invention, a battery for feeding electric power to the visible optical means is incorporated in the irradiation tube, and the irradiation tube is detachable from the X-ray generation unit. This irradiation tube can be used in an existing X-ray apparatus already installed in hospital. Further, the irradiation tube can be repaired or replaced easily.

According to the invention, a tube body of the irradiation tube is composed of a tube body base end, and a tip portion detachable at the tube body base end. A support piece projecting to the subject side is fixed at the tube body base end, and the tip can be fitted to the end portion of the tube body base end through this support piece, and the length projecting forward from the end portion at the tube body base end of the support piece is selected to be a value that insures a permissible distance SSD (source-skin distance) between the X-ray tube focus and the irradiation surface of the subject. Therefore, even if the X-ray is emitted without fitting the tip to the tube body base end, at least the permissible distance SSD is maintained. As regards this distance SSD, the minimum value of the exposure skin distance from the X-ray tube focus permitted for an output voltage of an X-ray apparatus is designated in various X-ray standards such as IEC Publication 407 Radiation Protection in Medical X-ray Equipment 10 kV to 400 kV. X-ray irradiation from a distance shorter than this set value is not permitted. In the invention, such risk can be avoided.

In the invention, a medical X-ray apparatus comprises a tube body having a hollow part for allowing an invisible electromagnetic wave, such as X-ray, ultraviolet ray, infrared ray and laser light to pass, and a plurality of visible optical means surrounding the hollow part at intervals in the peripheral direction of the tube body. Each visible optical means generates a visible light in a plane form including the axis of invisible electromagnetic wave passing through the hollow part. This visible light in a plane form allows the irradiation position of invisible electromagnetic wave to be indicated on the irradiation plane. Therefore, in the treatment with invisible laser light or radiation, the irradiation can be accurately focused on the target site of the body of the patient to be treated.

In the invention, each visible optical means comprises a light source and a lens for focusing the visible light from the light source in a plane form. In such constitution, spreading of visible light beam in the direction orthogonal to the optical axis is decreased, and the visible light beam is emitted nearly in the same size over the specified width in the optical axis direction, so that the irradiation position of invisible electromagnetic wave can be displayed accurately. Therefore, if the irradiation position is not a uniform circle such as the human face, distortions of the shape of visible light due to undulations of the irradiated plane can be minimized. The irradiation position of the invisible electromagnetic wave can accurately be shown to the radiologist.

In the invention, the visible light emitted by each visible optical means is designed to intersect the axis of invisible electromagnetic wave. The radiologist can recognize the irradiation field, at the position of the axis of invisible electromagnetic wave on the irradiation plane, as being symmetrical about the intersecting point of the visible light beam. The irradiation position of the invisible electromagnetic wave can be indicated more accurately.

According to the invention, an operation switch is provided on the outer circumference of the tube body, and when this operation switch is turned on, the light source is lit up for a predetermined period of time. The radiologist does not have to turn off the operation switch, which makes the operation simple, while wasteful power consumption of each light source is precluded. Also, the irradiation position of invisible electromagnetic wave can be set easily, accurately, and in a short time.

In the invention, since each light source is, for example, composed of a light-emitting diode, the constitution is very simple as compared with that using, for example, a semiconductor laser oscillator. Thus, the invention may be realized at a low cost, and the manufacturing cost can be reduced.

Also in the invention, the lapse of specific time is measured, after start of energization, in a timer circuit for generating pulses at specific time intervals. While the timer circuit is generating pulses, the switching circuit feeds power to illuminate the light source, and when the pulse output of the timer circuit is over, power being fed to the light source and the timer circuit is stopped. As a result, when a certain period of time has passed after lighting of the light source, the light source goes off automatically. Simultaneously with extinguishing of the light source, the energization of the timer circuit stops. Thus, wasteful power consumption can be prevented.

Furthermore, a switching element simultaneously controls turning on or off i.e., the energization of the light source and the timer circuit. A starting circuit actuates the switching element and leaves it in a conductive state forcefully. A conduction holding circuit maintains the conduction of the switching element while the timer circuit is generating pulses, and the light source and the timer circuit are energized, and when the pulse output of the timer circuit is over, the switching element is cut off, and the energization of the light source and timer circuit stopped.

When the starting circuit is put in action, the switching element is set in a conductive state, and the light source lights up and the timer circuit starts to work. Even if the starting circuit stops thereafter, the conductive state of the switching element is maintained. Further, after lapse of specific time, the switching element is set in a cut-off state, and the light source is put out automatically. Further, simultaneously with the light source being extinguished, the energization of the timer circuit stops. Thus, wasteful power consumption can be prevented.

In the invention, lapse of specific time is measured, after start of energization, by a timer circuit that generates pulses at specific time intervals. A first switching element simultaneously controls turning on or off, i.e., the energization of the light source and the timer circuit. The starting circuit starts the first switching element and makes the element in a conductive state forcefully. A second switching element permits energization of the light source while the timer pulse is generating pulses. The first switching element maintains the conductive state while a current is flowing in the light source, and is cut off while no current is flowing into the light source. While the timer circuit is generating pulses, the second switching element is made conductive to light up the light source. When the pulse output of the timer circuit is over, the second switching element is cut off, and no current flows into the light source, thereby disconnecting the first switching element.

When the starting circuit is put in action, the first switching element is set in a conductive state, the timer circuits starts generating pulses, and consequently the second switching element is also set in a conductive state, and a current flows into the light source to illuminate it. Afterwards, even if the starting circuit stops, the conductive state of the first switching element is maintained. After lapse of specified time, the second switching element is made in a cut-off state, and the light source goes out automatically. Furthermore, simultaneously with the light source being extinguished, the current flowing into the first switching element decreases, and the first switching element is cut off. Since the energization of the timer circuit stops, wasteful power consumption can be prevented.

In the invention, by using a thyristor as the first switching element, the function of maintaining a conductive state when a current greater than a predetermined current persists, and of maintaining a cut-off state when the current becomes less than the predetermined current can be realized easily in a small device.

According to the invention, by using an automatic reset time switch in the starting circuit, the switching element can be started only by the operator s touching the switch. The switch is then reset automatically, so that the manipulation for turning off the switch is not necessary, thereby facilitating the lighting operation of the light source.

In the invention, since the power source can be a battery, the light source control circuit can be operated independently of the power source system. A light source control circuit and an apparatus incorporating it can be carried easily. It is also easy to replace the irradiation tube of the invention with that assembled in an existing X-ray apparatus.

In the invention, since a constant current circuit for actuating the light source with a constant current is provided in an X-ray apparatus, a constant current flows into the light source, and the light quantity of the light source is stabilized.

By incorporating a light source control circuit in the irradiation tube of the invention, it enables one skilled in the art to obtain a lightweight, small-size X-ray irradiation tube excellent in controllability, small in power consumption, and capable of obtaining a stable quantity of light.

DETAILED DESCRIPTION OF THE PREFERRED EMBODIMENTS

Now referring to the drawings, preferred embodiments of the invention are described below.

Figure 2:
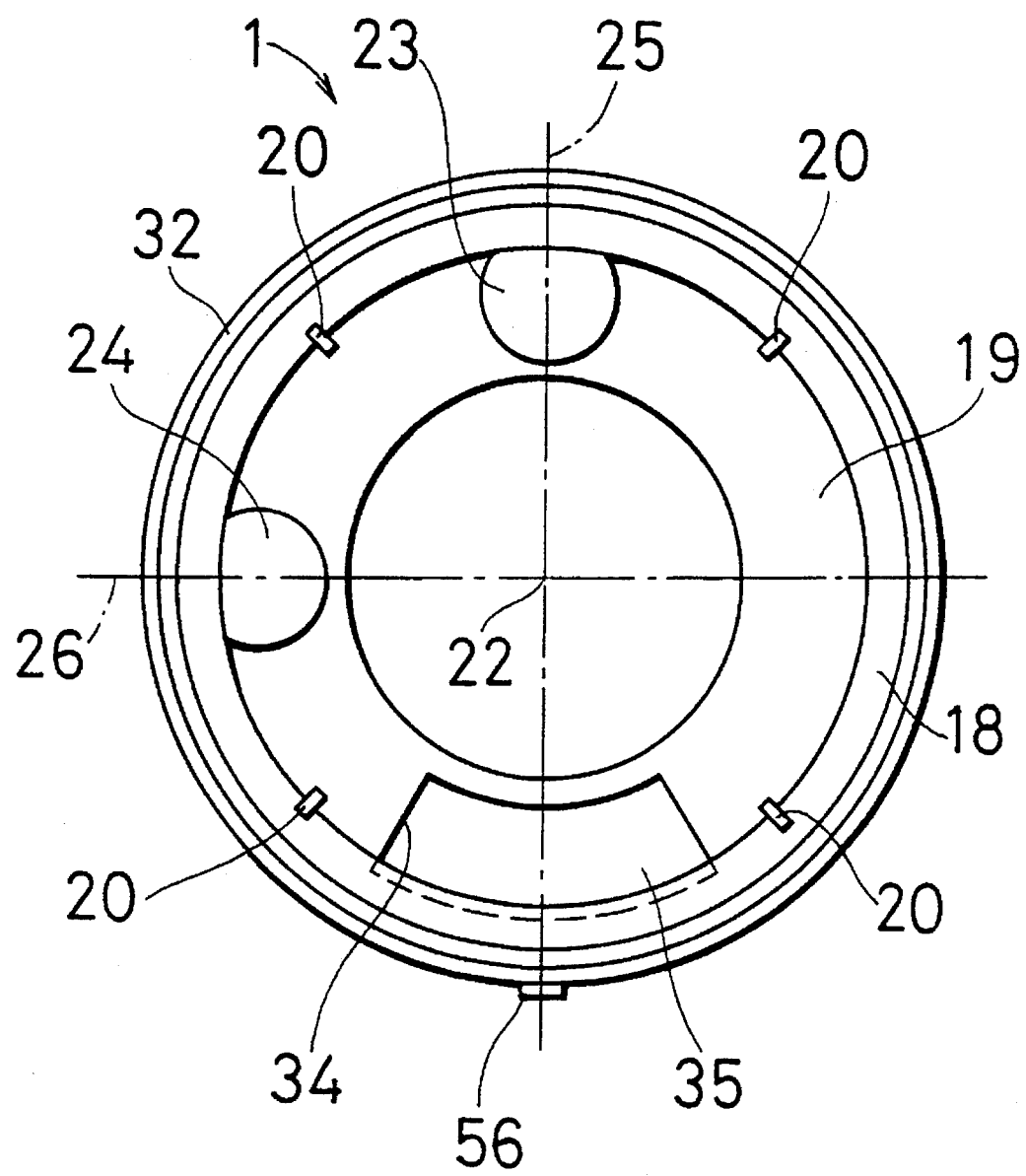
FIG. 2 is a front view of the irradiation tube as shown in FIG. 1.

FIG. 1 is a sectional view showing an irradiation tube 1 and an X-ray generation unit 2 incorporating the tube in an embodiment of the invention, FIG. 2 is a front view, as seen from the right side in FIG. 1, of the irradiation tube. An X-ray generated from the X-ray generation unit 2 is formed in a radiation cone and is guided by the irradiation tube 1.

Figure 3:
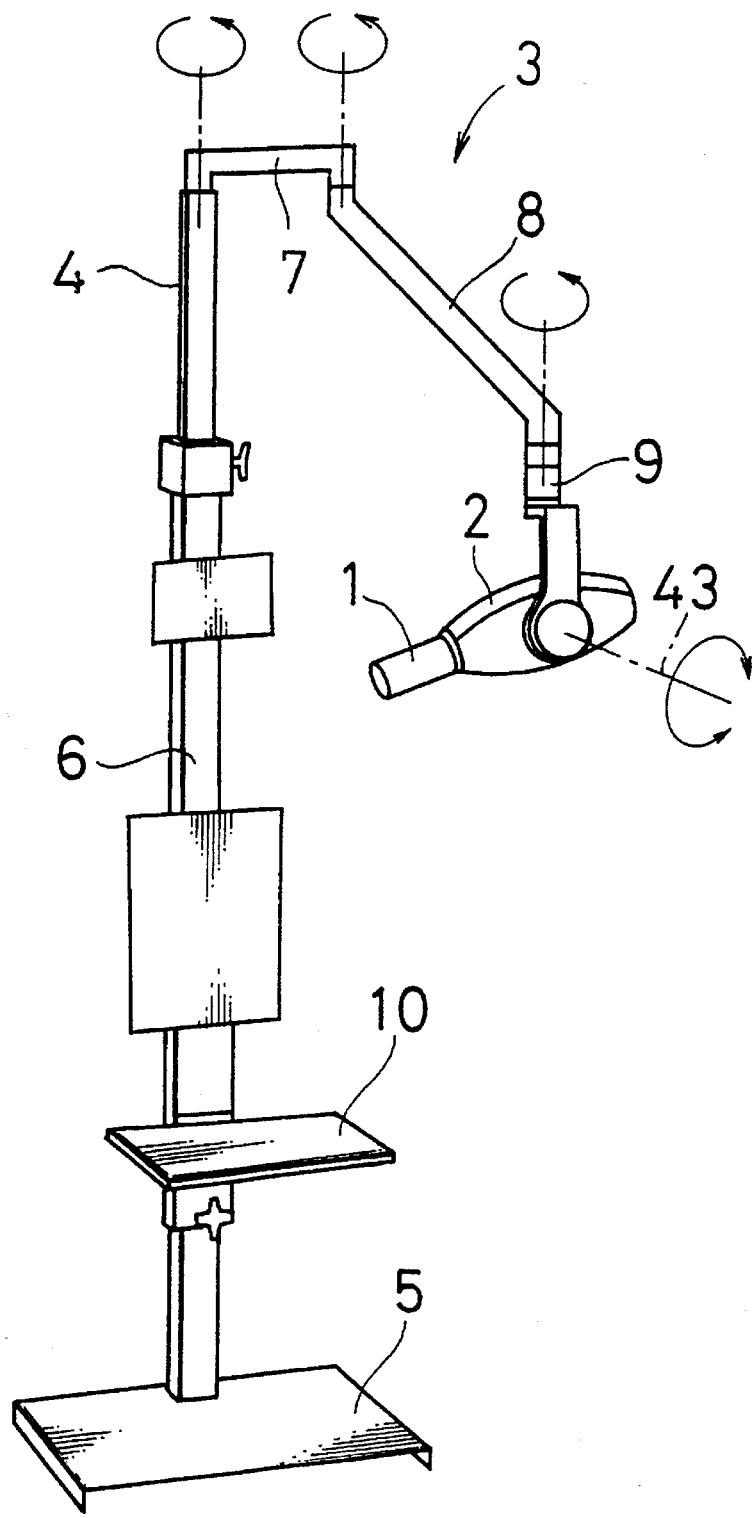
FIG. 3 is a perspective view showing an entire construction of a dental X-ray apparatus of the invention.

FIG. 3 is a perspective view showing a general feature of a dental X-ray apparatus 3 for oral radiography. An X-ray apparatus main body 4 possesses arms 7, 8, 9 angularly displaceable about the vertical axis, on a post 6 disposed on a base 5. A film or X-ray detection sensor is placed in the mouth of the patient sitting on a seat 10 of the post 6, and the irradiation tube 1 is brought close to the face of the patient so as to be opposite to a radiographic means. The X-ray generation unit 2 is positioned so that the sighting beam emitted from the irradiation tube 1 may be located at a specified position and in a specified direction, and the X-ray is generated after adjusting the configuration of the X-ray irradiation field and the radiographic means.

The X-ray apparatus of the invention may be either of a stationary type as shown in FIG. 3, or of a ceiling suspended type, wall mount type, or mobile type having the base 5 equipped with wheels.

Referring again to FIG. 1, in the X-ray generation unit 2, an X-ray tube 11 is contained in a case 12, and this case 12 is packed with insulating oil or the like. The case 12 is fixed in a housing 13, and a mounting member 14 is fixed to an X-ray opening 63 in the case 12. Inside the mounting member 14, a diaphragm 15 made of lead or similar material is fixed, and thereby, the X-ray from the focus F of the X-ray tube 11 is formed in a radiation cone 16, and the radiation cone 16 is guided by the irradiation tube 1, and is emitted to the exposure surface such as the skin surface of the patient which is the exposure subject at the right side in FIG. 1.

The irradiation tube 1, basically, possesses an irradiation tube main body 17 and a tip 18. The irradiation tube main body 17 possesses a tube body base end 19 fitted to the housing 13, and the tip 18 is detachably mounted with a support piece 20 to an exposure subject side end 19a of the tube body base end 19. The tube body base end 19 and the tip 18 compose a tube body 21.

In the tube body base end 19 of the irradiation tube main body 17, a plurality of visible optical means 23, 24 are disposed outside of the X-ray radiation tube 16, as shown in FIG. 2, at intervals in the peripheral direction around an X-ray axis 22. In this embodiment, two visible optical means 23, 24 are disposed at intervals of 90 degrees in the peripheral direction. One visible optical means 23 generates visible light 25 in a plane form that includes the axis 22 of X-ray on the exposure subject side. The other visible optical means 24 generates visible light 26 in a plane form that includes the axis 22 of X-ray. Therefore, these plane-form visible lights 25, 26 intersect on the axis 22 of X-ray. The intersecting position of these plane-form visible lights 25, 26 is always present on the axis 22 of X-ray. When these visible lights 25, 26 are emitted to the surface of the exposure subject, the intersecting position indicates the axis 22 of X-ray. The radiologist, when positioning the X-ray generation unit 2, can recognize the axis 22 of X-ray, that is, the center of irradiation field always with excellent visibility, regardless of the permissible distance SSD between the focus F of the X-ray tube 11 and the exposure skin surface of the patient which is the irradiation plane of the exposure subject as well as regardless of an angle between the exposure surface and the axis 22 of X-ray. Thereby, the positioning performance may be drastically improved. The irradiation tube main body 17 comprises the tube body base end 19, visible optical means 23, 24, a battery 31, a flat switch 32, a start circuit 33, and a lid 35. The axis 22 of X-ray coincides with the axis of the irradiation tube 1.

Figure 4:
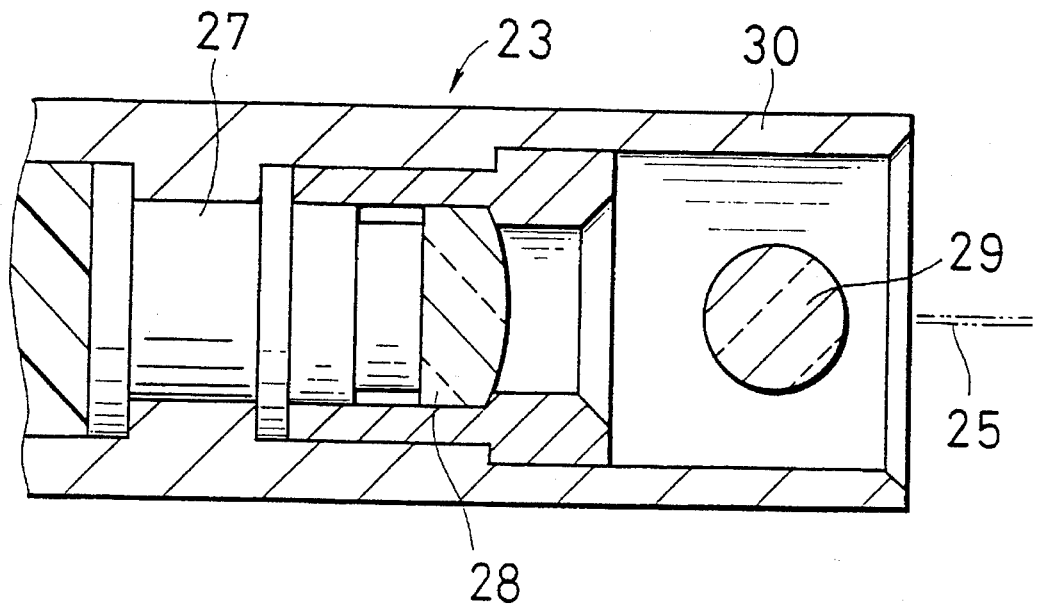
FIG. 4 is a sectional view of visible optical means according to the invention.

FIG. 4 is a sectional view of the visible optical means 23, and the other visible optical means 24 is also constructed in the same way as is the visible optical means 23. A visible light laser diode 27 generates a visible light with a wavelength of, for example, 650 to 830 nm. The visible light is focused by a plano-convex lens 28, and is further converted into a sector-shaped plane-form visible light 25 by a cylindrical lens 29 disposed ahead thereof. The laser diode 27 and lenses 28, 29 are integrally placed in a tubular case 30, and is stored in the tube body base end 19.

Figure 5:
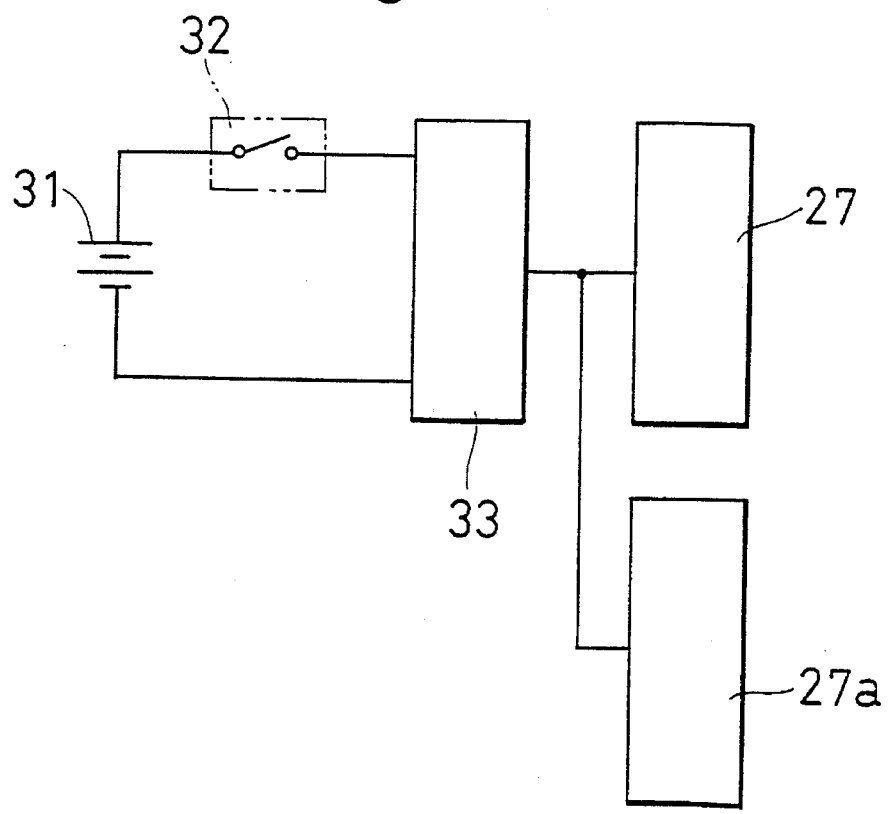
FIG. 5 is an electric circuit diagram corresponding to the visible optical means as shown in FIG. 4.

FIG. 5 shows an electric configuration relating to the laser diode 27. A laser diode provided in the visible optical means 24 is indicated by reference numeral 27a. The electric power from the battery 31 is applied to the start circuit 33 through the flat switch 32, and thereby, the laser diodes 27, 27a are actuated. The battery 31 is placed in a storing recess 34 in the tube body base end 19 shown in FIG. 2, and is sealed by the lid 35. The start circuit 33 is assembled in the case 30 of the visible optical means 23.

Figure 6:
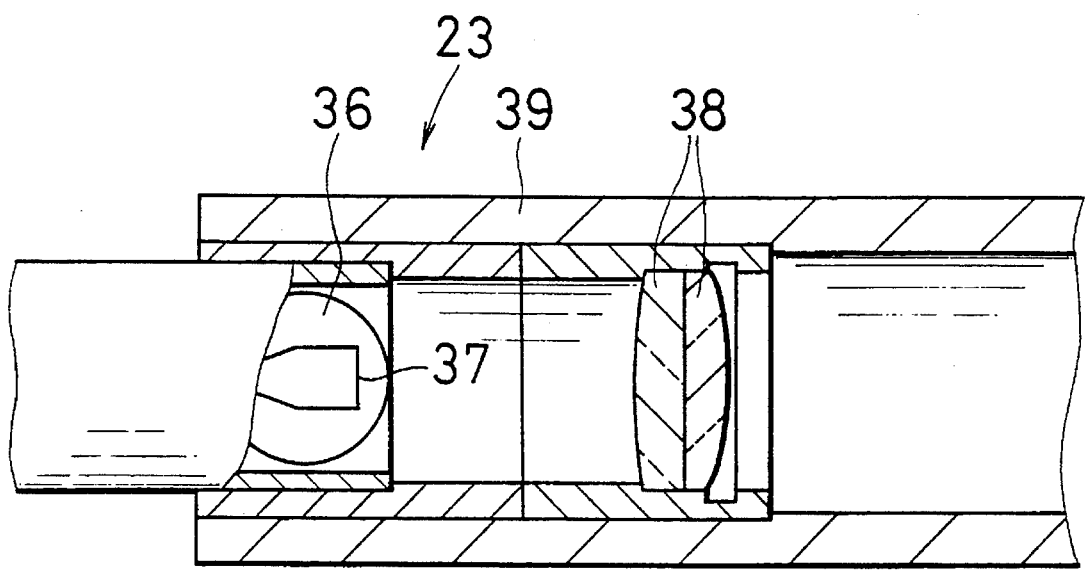
FIG. 6 is a sectional view of visible optical means in another embodiment of the invention.

FIG. 6 is a sectional view of the visible optical means 23 used instead of the constitution shown in FIG. 4. The visible optical means 23 shown in FIG. 6 has an incandescent light 36, and this incandescent light 36 includes a linear filament 37. The axis of the lineal filament 37 corresponds to the plane of the visible light 25 in a plane form, and the upper and lower lines in FIG. 6 including the axis of the filament 37 pass through the axis 22 of X-ray. The incandescent light 36 is also supplied with electric power from the battery 31 through the flat switch 32. Ahead of the incandescent light 36, a focusing lens 38 is disposed. The lens 38 may be either a combination of two plano-convex lenses as shown in FIG. 6 or two convex lenses, and the incandescent light 36 and lens 38 are placed in a tubular case 39. The other visible optical means 34 may be constructed in the same way as shown in FIG. 6.

In another embodiment of the invention, the visible optical means 23, 24 may be formed by combination of a light source for generating visible light, a lens, and a light shielding diaphragm having slits for forming plane-form visible lights 25, 26, or may be constituted differently.

Since the battery 31 and the start circuit 33 can be stored in the tube body base end 19 of the irradiation tube 1 and this irradiation tube is detachably fitted to the X-ray generation unit 2 by means of bolts 56, the irradiation tube can easily be installed in an existing X-ray apparatus. In other embodiments of the invention, the battery 31 or other power source may be connected, for example, from a low voltage circuit of the X-ray generation unit 2.

Figure 7:
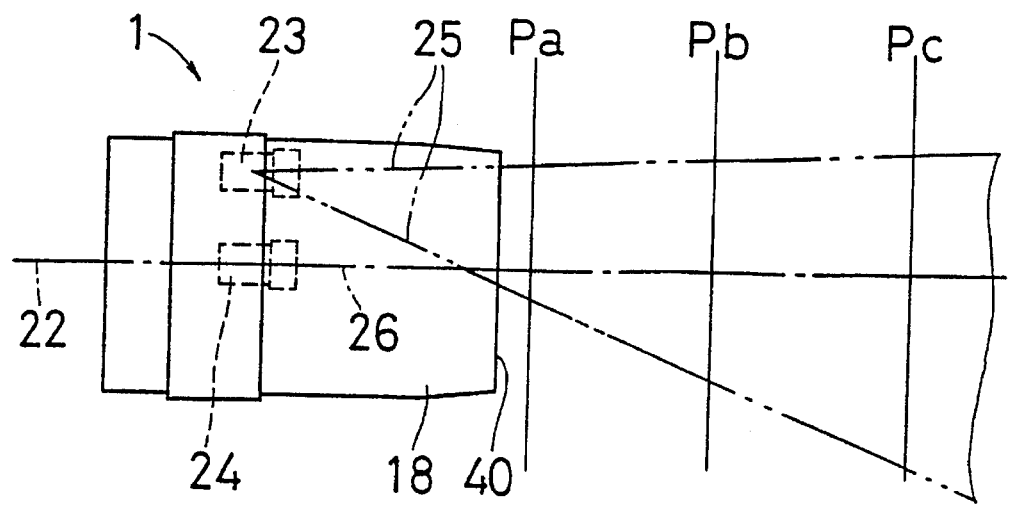
FIG. 7 is a simplified side view showing the manner in which plane-form visible lights are irradiated by visible optical means in the practice of the invention.
Figure 8:
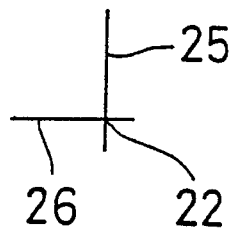
FIG. 8(1), 8(2), 8(3) are diagrams showing an optical pattern on a irradiated plane vertical to the axis of X-ray at plural positions along the axis as shown in FIG. 7.
Figure 8:
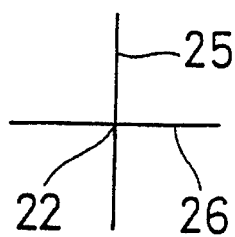
Figure 8:
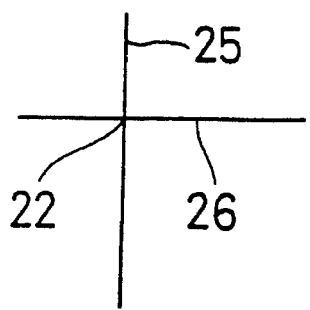

FIG. 7 is a simplified view of visible lights 25, 26 in a plane form emitted from the visible optical means 23, 24 of the irradiation tube 1. When the surface of the exposure subject is illuminated by visible lights, a thin linear optical pattern is drawn. In this embodiment, two visible lights 25, 26 of sector-shaped beam are generated on the periphery of the tube body base end 19 at positions 90 degrees apart, and the optical patterns on the surface of the exposure subject at plural positions pa, pb, pc along the axis 22 of X-ray are as shown in FIGS. 8(1), 8(2), and 8(3), respectively. In such cross-shaped optical patterns, regardless of the irradiation position and angle ahead of (right side in FIG. 7) of the end 40 of the tip 18, the intersecting point of the visible lights 25, 26 always indicates the center of the radiation cone 16 of X-ray. In other embodiments of the invention, other than the cross-shaped visible optical pattern, more sector-shaped visible light beams may be generated, and the intersecting point of these plane-form visible lights may be matched with the axis 22 of X-ray.

The flat switch is in a form of tape or sheet as shown in FIGS. 1 and 2, and is constituted so as to surround the tube body base end 19 of the irradiation tube main body 17 entirely in the peripheral direction. Accordingly, the radiologist, when positioning the radiographic position in an actual clinical operation, can effect positioning easily without paying attention to the operation of the flat switch 32 by the finger of the radiologist. This flat switch 32 is disposed along a part of the axis of the irradiation tube main body 17, but in another embodiment of the invention, the area of the flat switch 32 may include the region that the radiologist touches spontaneously when positioning, and preferably may extend in a wider area. The switch 32 may be composed to cover the entire outer circumference of the irradiation tube main body 17.

The reason of the use of on/off control of the visible optical means 23, 24 by manipulating the flat switch 32 in this manner is to alleviate the glare felt by the patient by emitting the visible light only for a moment and by finishing positioning in a very short period of time, for fear that the visible lights 25, 26 should cross the eyes of the patient depending on the radiographic position. Besides, by installing the flat switch in the irradiation tube of the X-ray generation unit and/or in the rear part, the flat switch can be manipulated at the hand position of the radiologist when positioning the X-ray generation unit to the exposure subject. In a further embodiment of the invention, without the flat switch 32, the visible optical means 23, 24 may be lit up continuously.

In the foregoing embodiment, the flat switch 32 is interposed between the battery 31 and the start circuit 33 for the purpose of on/off controlling electric power. In other embodiments of the invention, as will be described later, a control signal for on/off control may be applied to a processing circuit of a microcomputer or the like, and the start circuit 33 may be controlled by this processing circuit to control the laser diodes 27, 27a. The flat switch 32 may be formed of a pressure sensitive sheet, membrane switch, and etc, and is capable of generating an electric signal by being touched or pressed. The switch can be made of a metal plate and the like, and may be constituted differently.

Figure 9:
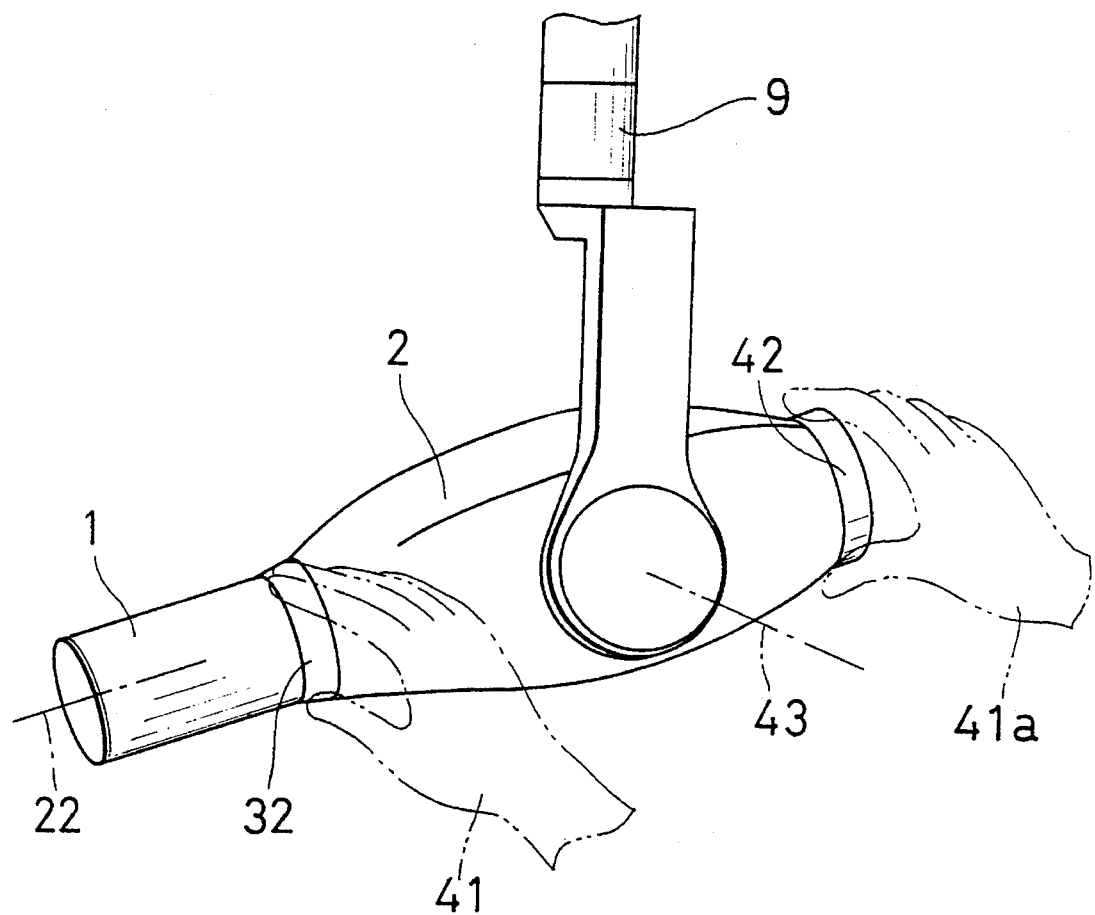
FIG. 9 is a perspective view showing how a flat switch is disposed in an X-ray generation unit according to a further embodiment of the invention.

FIG. 9 is a perspective view of a different embodiment of the invention. In the X-ray generation unit 2, the flat switch 32 is provided as described above. The flat switch 32 can be manipulated by a hand 41 of the radiologist while positioning the X-ray generation unit 2. Another flat switch 42 can be provided in the X-ray generation unit 2, and positioning and switch manipulation can be done by the other hand 41a. The arm 9 is provided with the X-ray generation unit 2 such that the unit can be angularly displaceable about a horizontal rotational axis 43 that orthogonally intersects the axis 22 of X-ray. In this embodiment, the rotational axis 43 passes through the axis 22 of X-ray. The flat switches 32, 42 are disposed in the direction of the axis 22 of X-ray around the rotational axis 43 at both sides thereof e.g., in the rear part of the irradiation tube 1 and X-ray generation unit 2, respectively. Controllability is thus enhanced. The flat switch 32 may be disposed in the rear part of either the irradiation tube 1 or the X-ray generation unit 2.

Referring back to FIG. 7, the tip 18 is designed to secure a distance between the focus F of the X-ray tube 11 and the end 40 of the tip 18 when the end touches the exposure surface of the patient, which distance is required to be greater than the permissible distance SSD. The tip can be made of a light permeable material, such as transparent glass, lead glass, acrylic resin, vinyl chloride, and other transparent materials. When the end 40 of the tip 18 is brought to a closest distance to the exposure surface, which is the irradiation surface of the patient, e.g., in a abutting state, the cross-shaped visible light pattern may be observed from the exterior of the tip 18 as shown in FIG. 8. The exposure center of the X-ray can thus be determined accurately, which makes accurate positioning possible. Moreover, by bringing the exposure area closer to the X-ray tube 11 within a range required by the permissible distance SSD, the conical expansion of the exposure region can be minimized. The tube body base end 19 may be either made of a light permeable material in the same way as is the tip 18, or made of a light shielding material.

Figure 10:
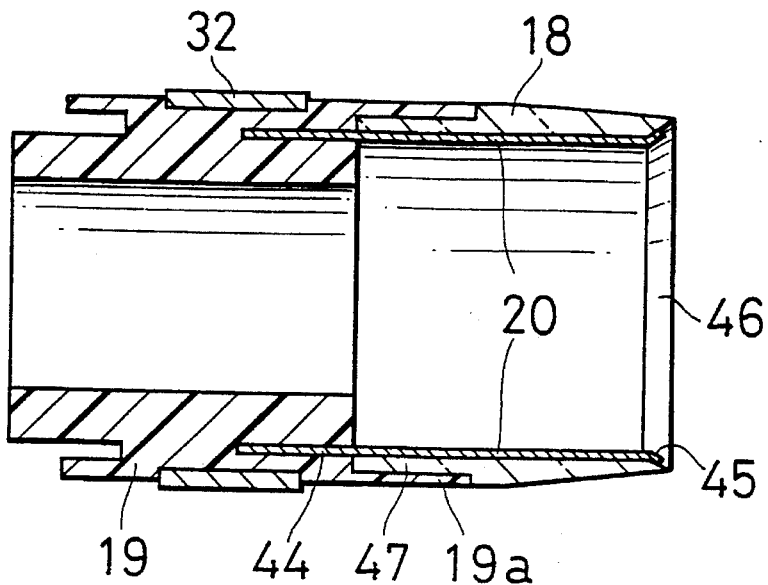
FIG. 10 is a simplified sectional view showing how a tube tip portion of an irradiation tube is supported by a support piece according to the invention.

FIG. 10 is a simplified sectional view showing a support piece 20 that supports the tip 18 which is detachable from the tube body base end 19. A plurality (four in this embodiment) of support pieces 20 are provided at equal intervals in the peripheral direction of the tube 1. A base end 44 is buried in the tube body base end 19, and is composed of a spring material having an elastic force, for example, a piano wire. A front end 45 of the support piece 20 is bent outward in the radial direction thereof, and it is elastically arrested on a stopping surface 46 in a circular truncated cone shape which expands outward in the radial direction as it projects forward, near the end 40 of the tip 18, thereby preventing the tip 18 from dislocating from a fitting part 47 of the end 19a of the tube body base end 19.

Figure 11:
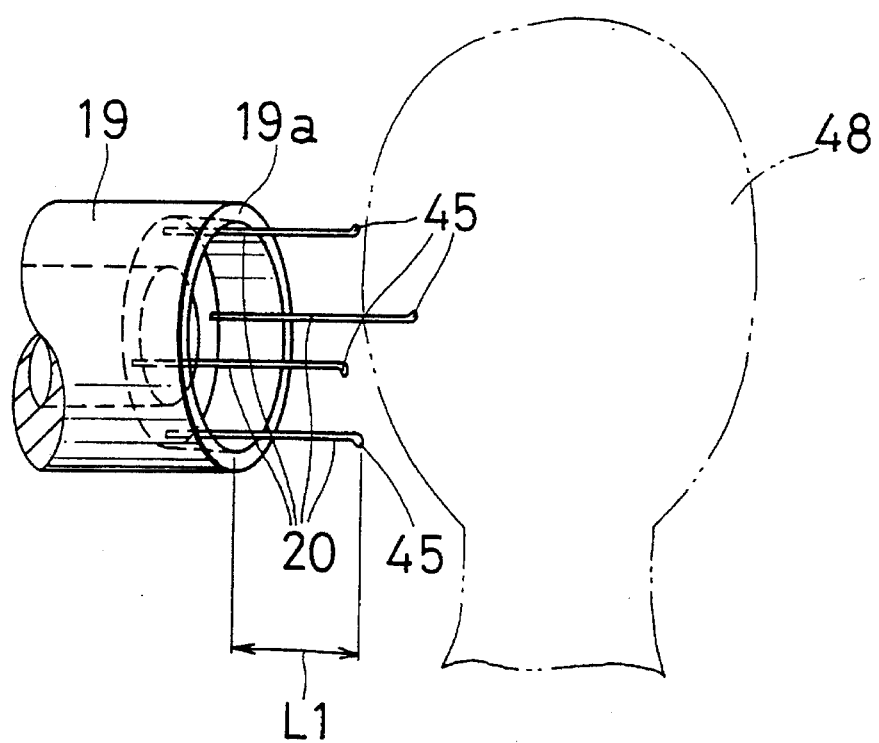
FIG. 11 is a perspective view showing the state of separating a tube tip portion from a tube body base end according to the invention.

When the support piece 20 is in a natural state as shown in FIG. 11 with the tip 18 removed from the tube body base end 19, the length L1 of the tube body base end 19 projecting from the end 19a to the front end 45 is selected to be a value which insures the permissible distance SSD between the focus F of the X-ray tube 11 and the irradiation surface 48 of the exposure subject, i.e., greater than the permissible distance SSD. Therefore, even if radiography is performed without installing the tip 18, the front end 45 of the support piece 20 faces against the irradiation plane 48, and the permissible distance SSD is thus maintained. If the tip 18 is screwed into the tube body base end 19, support pieces 20 are not provided. When the radiologist forgets to fit the tip 18, the end 19a of the tube body base end 19 faces against the irradiation plane 48, and the permissible distance SSD cannot be secured. In such a case, the subject is exposed to X-ray at a high X-ray intensity. The invention solves this problem.

Figure 12:
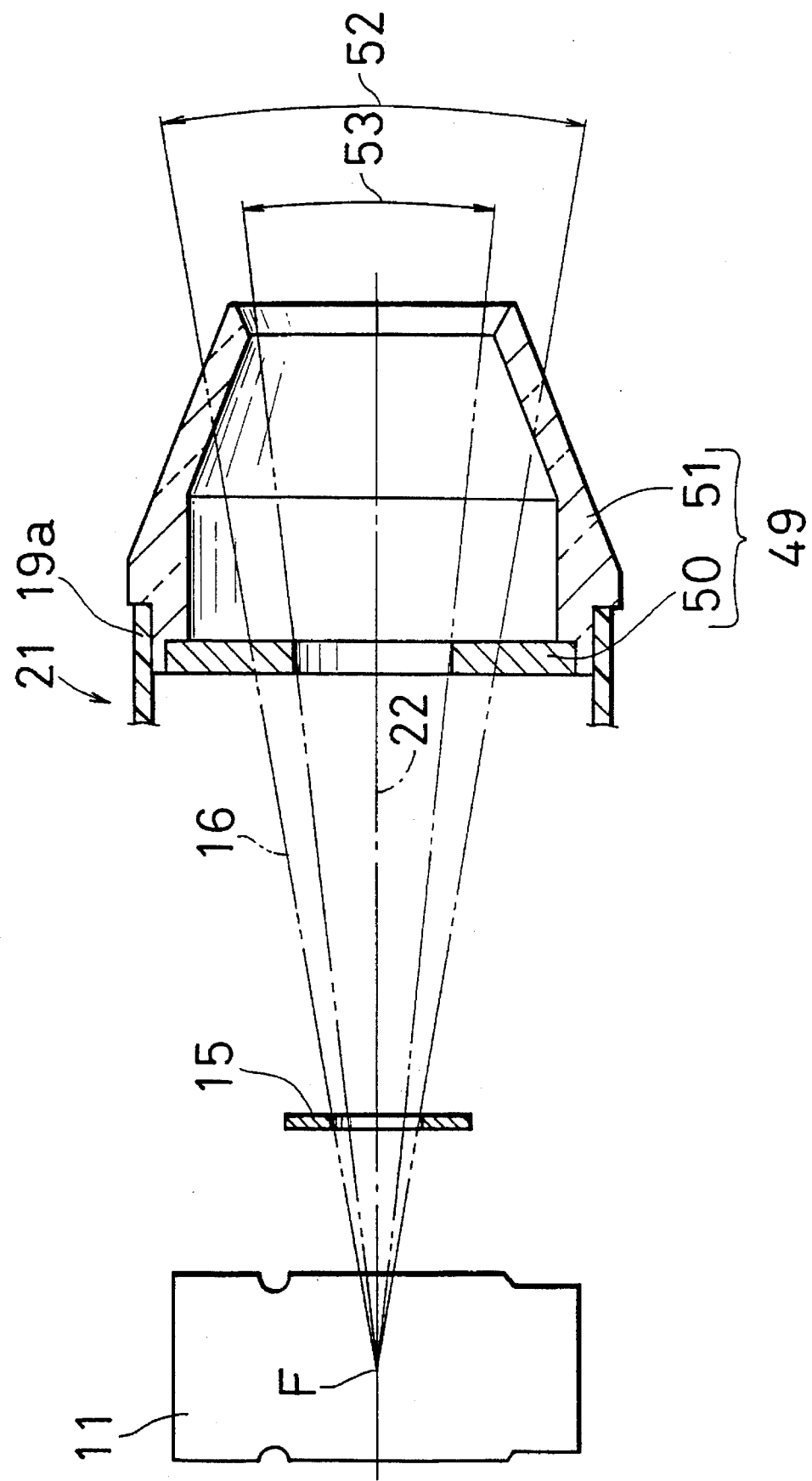
FIG. 12 is a sectional view showing a tube tip portion in a still further embodiment of the invention.

FIG. 12 is a sectional view showing a tip 49 in another embodiment which could replace the foregoing tip 18. When employing a film of 30×40 mm (film diagonal 50 mm) widely used at the present, the tip 18 with a relatively large inside diameter is used. When radiographing children, a smaller film of 22×30 mm (film diagonal 37.2 mm) must be used. If the tip 18 is also used in this case, an unnecessary exposure dose is given to the children. To solve this problem, it is advisable that a tip 49 having a secondary diaphragm 50 made of lead, antimony or other material fixed in the tube body main body 51 (as shown in FIG. 12) be employed. Such tip 49 is set aside separately from the tip 18, and is made available for instant replacement in the tube body base end 19. By using the tip 49, an irradiation field 53 smaller than the irradiation field 52 by the tip 18 can be achieved. Thereby, the exposure dose can be reduced. In FIG. 12, a constitution that keeps the permissible distance SSD may be provided in the same manner as does the support piece 20.

Figure 13:
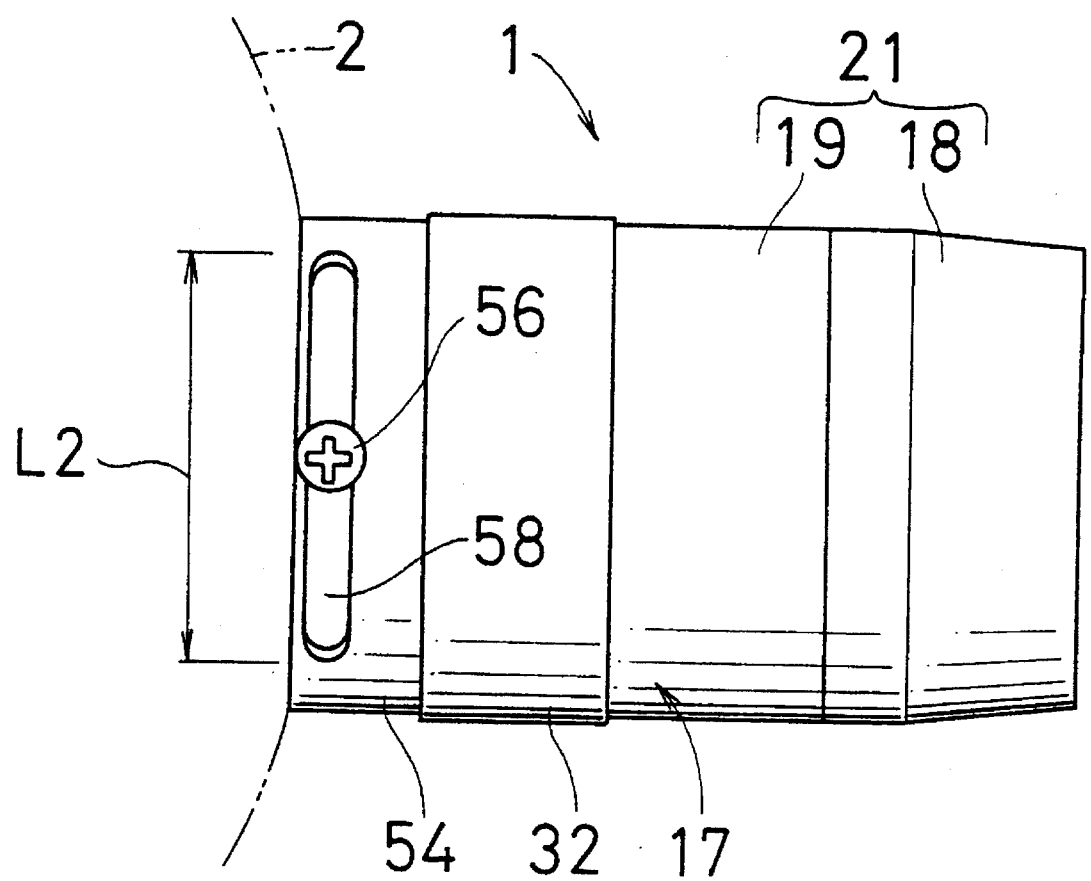
FIG. 13 is a bottom view of an embodiment of the invention, showing a construction for permitting angular displacement of an irradiation tube.

FIG. 13 is a bottom view of a part of the irradiation tube 1 and X-ray generation unit 2. The tube body base end 19 comprises the tube body 21 of the irradiation tube body main body 17. The base end 19 has a mounting member 14 of the X-ray generation unit 2 fitted in a part 54 closer to the X-ray generation unit 2. An end 55 of the housing 3 (see FIG. 1) fits in the part 54, and a shaft part 57 of a bolt 56 (FIG. 1) is slowly inserted into a slop 58 formed in the peripheral direction of the tube 54, and further inserted through a slot 59 similar to the slot 58. The shaft part 57 is screwed and fixed to the mounting member 14 of the X-ray generation unit 2. As shown in FIG. 1, the shaft part 57 further penetrates through a bolt insertion hole 60 having a circular section orthogonal to the shaft formed in the end 55 of the housing 13 of the X-ray generation unit 2. A head 61 of the bolt 56 partly covers the slot 58 of the tube 54. As a result, the tube body base end 19 is arrested in the motion in the direction of the axis 22 of X-ray, and at the same time is angularly displaceable along the length in the peripheral direction of the slot 58 about the axis 22. The length L2 along the peripheral direction of the slot 58 may exceed a value corresponding to the angle of the visible optical means 23, 24 in the peripheral direction, e.g., over 90 degrees in this embodiment.

In the tube body base end 19 of the irradiation tube body 17, the visible optical means 23, 24 are provided as described earlier. Therefore, while the intersection of the plane-form visible lights 25, 26 that indicates the center of irradiation field coincides with the axis 22 of X-ray, the plane-form visible lights 25, 26 can be rotated. In actual clinical operations, the radiologist can match the linear optical pattern with the radiographic reference line most suited to the radiographic position, so that the image reproducibility may be enhanced outstandingly. If the patient is hypersensitive to light, the visible light 25 or 25 can be offset from the eyes of the patient by angular displacement of the tube body base end 19. The patient may not feel glare, where the pain is alleviated.

Figure 14:
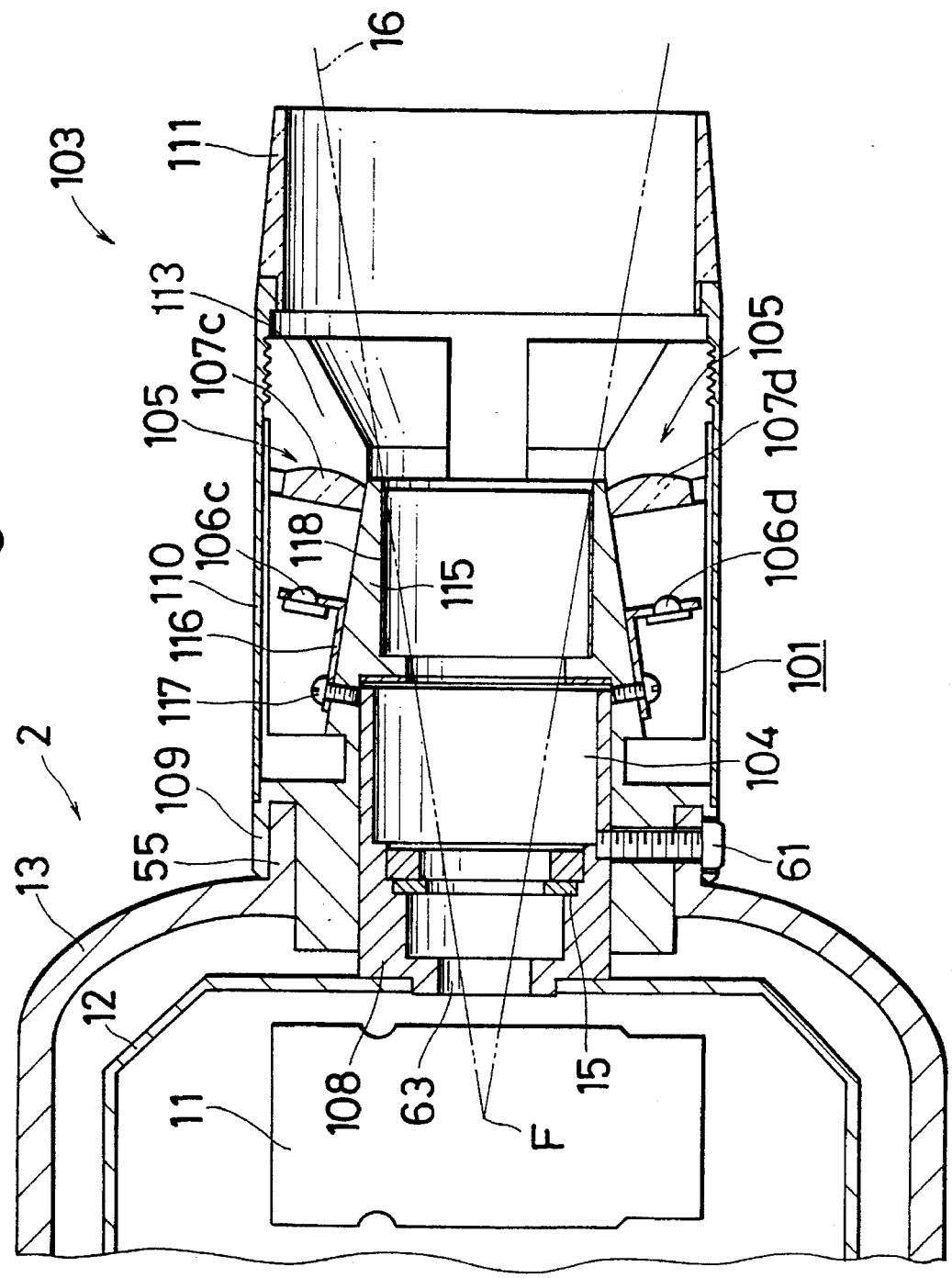
FIG. 14 is a sectional view showing a tube body and an X-ray generation unit on which the body mounted in yet another embodiment of the invention.
Figure 15:
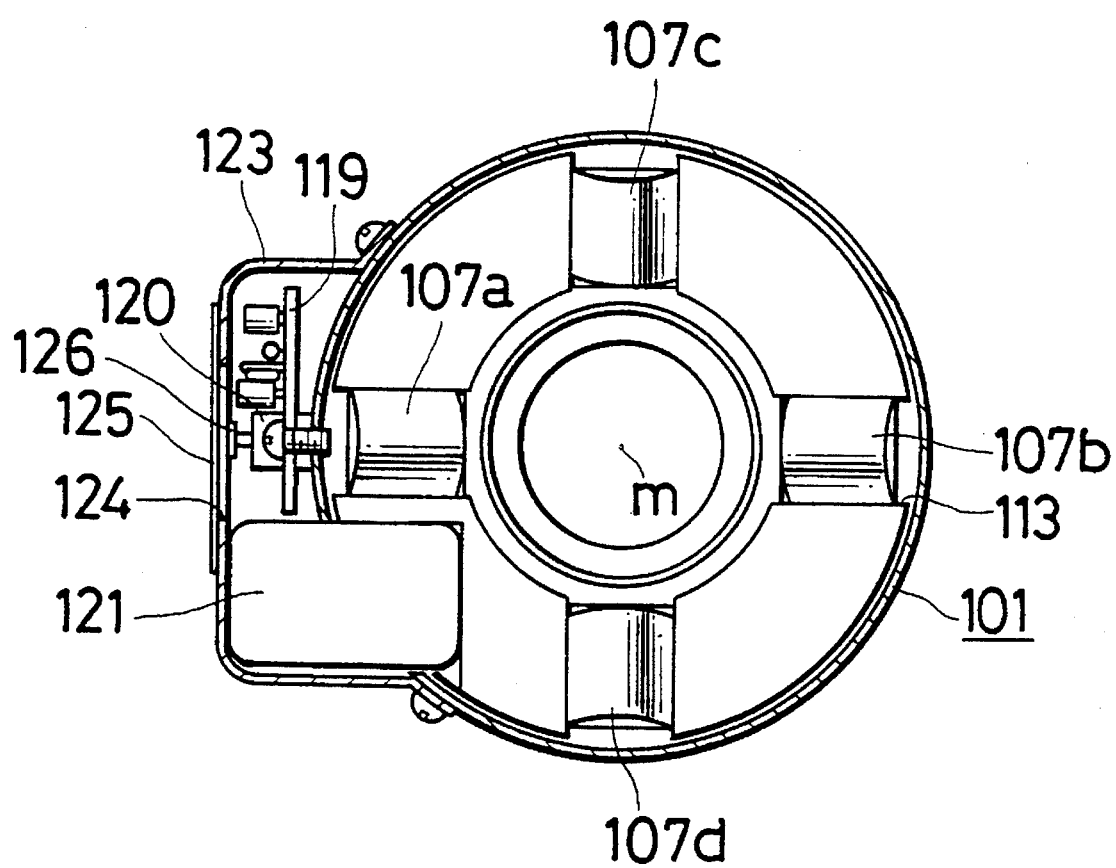
FIG. 15 is a sectional view of the tube body in FIG. 14 as seen from the right side thereof.

FIG. 14 is a sectional view showing a tube body 101 and an X-ray generation unit 2 wherein the tube body is detachably mounted in a further different embodiment of the invention. FIG. 15 is a sectional view of the tube body 101 as seen from the right side in FIG. 14. The X-ray generation unit 2 is the same as in the embodiments shown in FIGS. 1 through 13, and the same reference numerals are used to describe the corresponding parts. In the end 55 of the housing 13 of the X-ray generation unit 2, a medical position indicating apparatus 103 of this embodiment is installed. The medical position indicating apparatus 103, basically, comprises a tube body 101 fixed to the end 55 with bolts 61, and plural (four in this embodiment) visible optical means 105 provided at intervals in the peripheral direction, externally surrounding a hollow part 104 for defining a radiation cone 16 in the tube body 101. The visible optical means 105 include light-emitting diodes (LEDs) 106 as light sources, and cylindrical lenses 107. The light from the light-emitting diode 106 is focused on a plane including the optical axis of X-ray (invisible electromagnetic wave) from the X-ray tube 11 by the cylindrical lens 107. The visible optical means 105 are provided at an interval of 90 degrees in the peripheral direction of the tube body 101.

The tube body 101 is installed in the housing 13, and comprises a mounting member 108 for securing the diaphragm 15, a first tube 109 externally fitted to the mounting member 108 and installed in the end 55, a second tube 110 coaxially fixed on the first tube 109, and a light permeable tip 111 coaxially provided on the second tube 110. The first and second tubes 109, 110 are made of synthetic resin such as vinyl chloride, and the tip 110 is made of light permeable synthetic resin such as acrylic.

In the first tube 109, storage holes 113 for storing visible optical means 105 are formed at every 90 degree in the peripheral direction of the tube. The storage holes 113 and light-emitting diodes 116 are fixed on the outer circumference of the circular truncated cone portion 115 of the second tube 110 by means of almost L-shaped mounting pieces 116 and screws 117. On the inner circumference of the circular truncated cone portion 115, a right circular cylindrical sleeve 118 made of lead with a thickness of, for example, about 0.5 mm is installed, defining the radiation code 16 of X-ray.

FIG. 15 is a sectional view of the tube body 101. In the storage holes 113, cylindrical lenses 107a to 107d are stored, and generating lines of cylindrical lens 107a and cylindrical lens 107b (positioned diagonally) nearly coincide with those of each other, and similarly generating lines of cylindrical lens 107c and cylindrical lens 107d (positioned diagonally) nearly coincide with those of each other.

On the outer circumference of the tube body 101, a light source control circuit 119 for controlling light sources which correspond to the cylindrical lenses 107a to 107d is provided. The light source control circuit 119 is provided with a switch 120 for starting lighting of the light source. The light source control circuit 119 and a battery 121 for feeding electric power to the circuit are covered with a cover 123, and a penetration hole 124 is formed in the cover 123 immediately above the switch 120. Also, a flexible sheet 125, referred to as flush sheet, is provided further to cover the penetration hole 124. When the radiologist lights up the light source by pressing the sheet 125 by a finger, an operation piece 126 of the switch 120 is pressed through the sheet 125 with the switch 120 being conducted. Thus, the light source can be manipulated while keeping dust tightness and water proofness.

Figure 16:
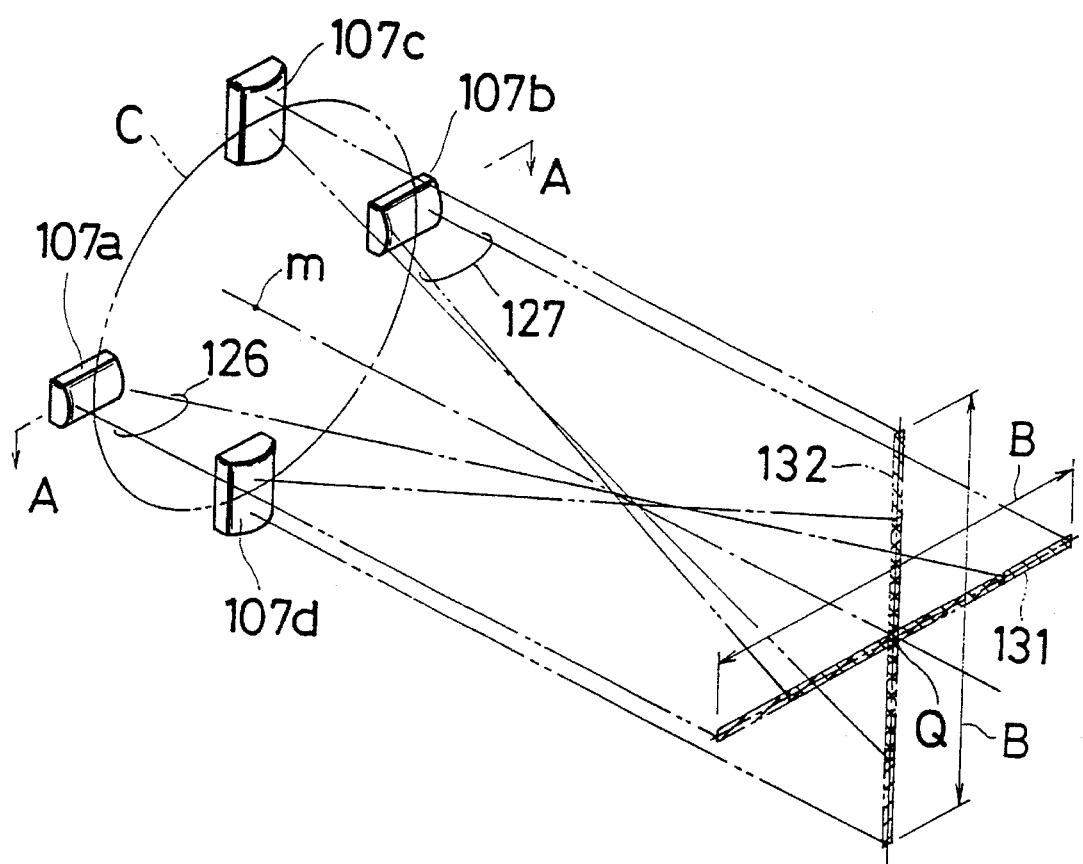
FIG. 16 is a diagram showing a configuration of cylindrical lenses according to the invention.

FIG. 16 is a diagram showing the arrangement of the cylindrical lenses 107. FIG. 17(a) is a simplified sectional view as seen from the section line A—A in FIG. 16. In the diagram, reference numerals 132Pa, 132Pb, 132Pc are optical patterns 132 as seen from the beam emitting direction at Pa, Pb, Pc, respectively. The cylindrical lenses 107 are disposed at an interval of 90 degree on a hypothetical circle C centered on optical axis m of X-ray. Referring to the cylindrical lenses 107a, 107b disposed symmetrically about the hypothetical plane including the optical axis m, one cylindrical lens 107a forms the light in a sector beam as indicated by reference numeral 126, while the other cylindrical lens 107b forms into a sector beam as indicated by reference numeral 127. The beams 126, 127 can form thin linear optical patterns 131, 132 of nearly the same width B on irradiation planes Pa, Pb, Pc at intervals in the direction of optical axis. FIG. 17(b) shows optical patterns 131, 132 at positions Pa, Pb, Pc along the optical axis m of X-ray. At positions Pa, Pb, Pc, optical patterns 131, 132 possess an intersection Q on the optical axis m of X-ray, and the size of the cross is always constant, being nearly the same as the X-ray irradiation region. Therefore, when positioning the X-ray irradiation position, even if the distance from the exposure surface varies, the optical patterns 131, 132 are hardly extended. Since these optical patterns 131, 132 illuminate the area nearly the same size as the actual X-ray irradiation region, inconvenience such as cone-cut can be eliminated.

In the foregoing embodiment, the cylindrical lenses 107a, 107b adjacent in the horizontal direction are explained. The same applies to cylindrical lenses 107c, 107d adjacent in the vertical direction.

Figure 18:
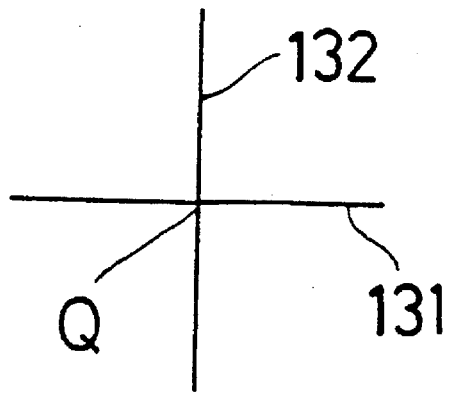
FIG. 18(1),18(2),18(3) are diagrams illustrating the shape of irradiation patterns displayed on a subject surface according to the invention.
Figure 18:
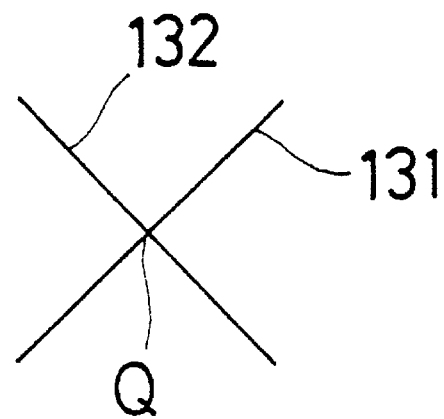
Figure 18:
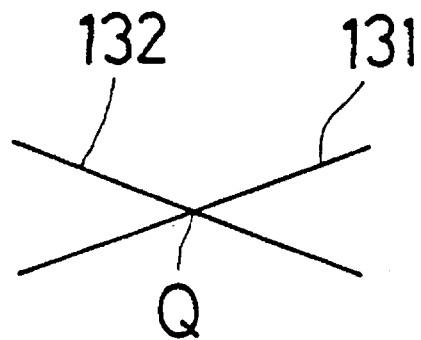

In another embodiment of the invention, the irradiation pattern of visible light is not limited to the cross form shown as in FIG. 18(1), but may be an X-form as shown in FIG. 18(2), or two optical patterns 131, 132 may be crossed at an angle other than right angle as shown in FIG. 18(3). By forming the optical patterns 131, 132 on the exposure surface in a horizontal line (–) which extends in the horizontal direction, the invention may be practiced also when positioning the X-ray irradiation position on the occlusion plane of the patient at the time of whole-jaw general-view X-ray filming referred to as panorama. Further, by forming the optical patterns in a vertical line (|) which extends in the vertical direction, infrared ray or ultraviolet ray may be accurately emitted to a lesion in the longitudinal direction for treatment.

Figure 19:
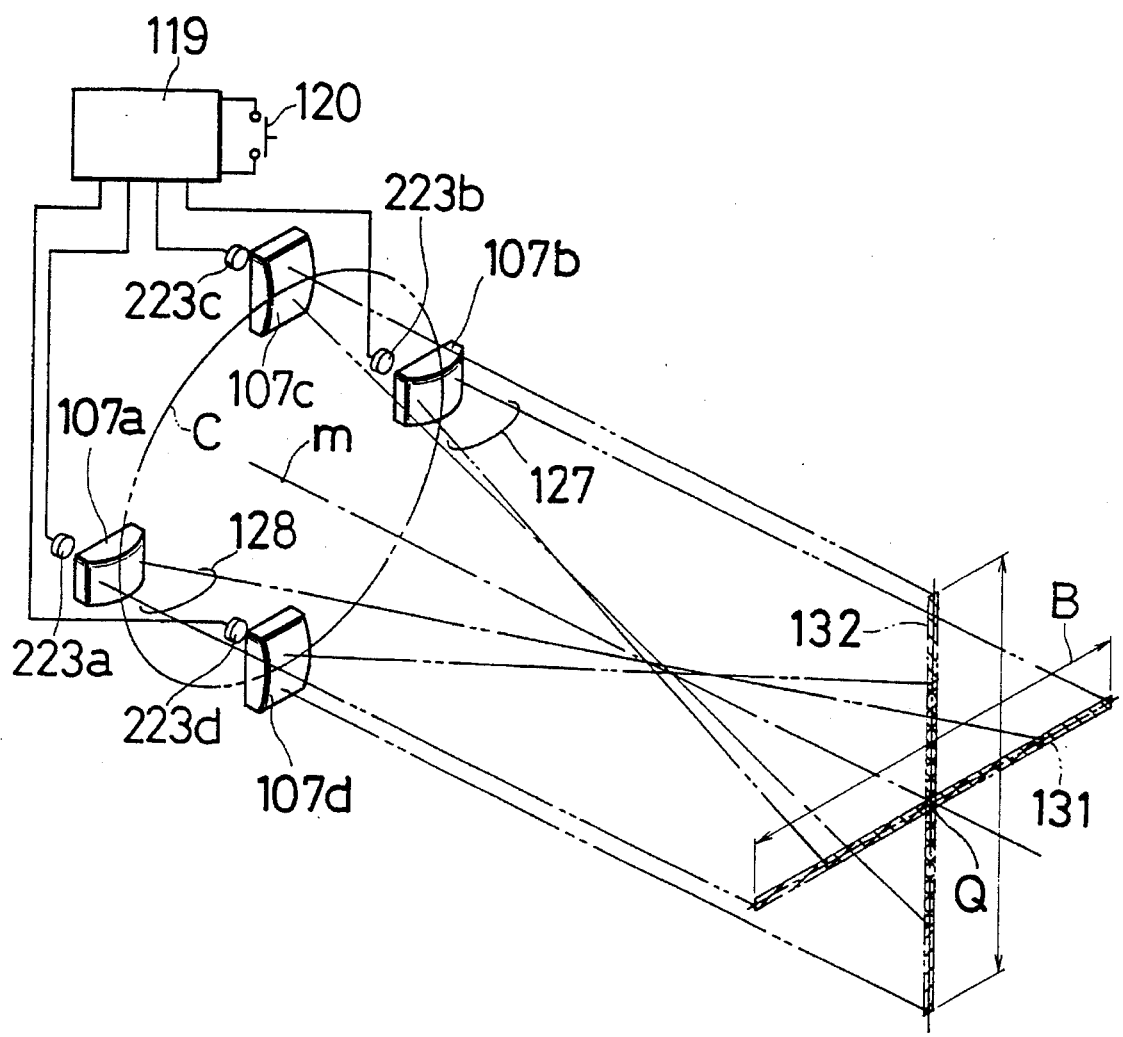
FIG. 19 is an illustrative diagram of an optical system configuration having a light source control circuit of the invention included in the cylindrical lenses shown in FIG. 16.

FIG. 19 is an optical arrangement of the irradiation tube 1 as shown in FIG. 15. The cylindrical lenses 107a to 107d are disposed at an interval of 90 degree on a hypothetical circle C, and at positions focused by the cylindrical lenses 107a to 107d, light sources 223a to 223d such as LED (light-emitting diode), LD (laser diode), and incandescent light are disposed at an interval of 90 degree. The light sources 223a to 223d are actuated by a light source control circuit 119 driven by a switch 120.

For example, the visible light emitted from the light source 223a is focused in the vertical direction by the cylindrical lens 107a, and is converted into a sector beam 128. Similarly, the visible light emitted from the light source 223b is also focused in the vertical direction by the cylindrical lens 107b, and is converted into a sector beam 127. The beams 127, 128 are imaged at imaging positions apart by a specific distance, and forms a composite horizontal slit image 131. Similarly, in the case of the light sources 232c, 232d, visible light focusses in the horizontal direction through the cylindrical lenses 107b, 107d and are converted into a sector beam, and a vertical slit image 132 is formed at the imaging position. The slit images 131, 132 of line segment length B cross orthogonally and divide each other into two equal portions, thereby forming a cross slit image. The intersection Q coincides with the central axis m of the X-ray flux. In this way, the cross slit image of visible light is formed so as to coincide with the X-ray irradiation field. The radiologist can clearly recognize the range and central position of the X-ray irradiation field.

Figure 20:
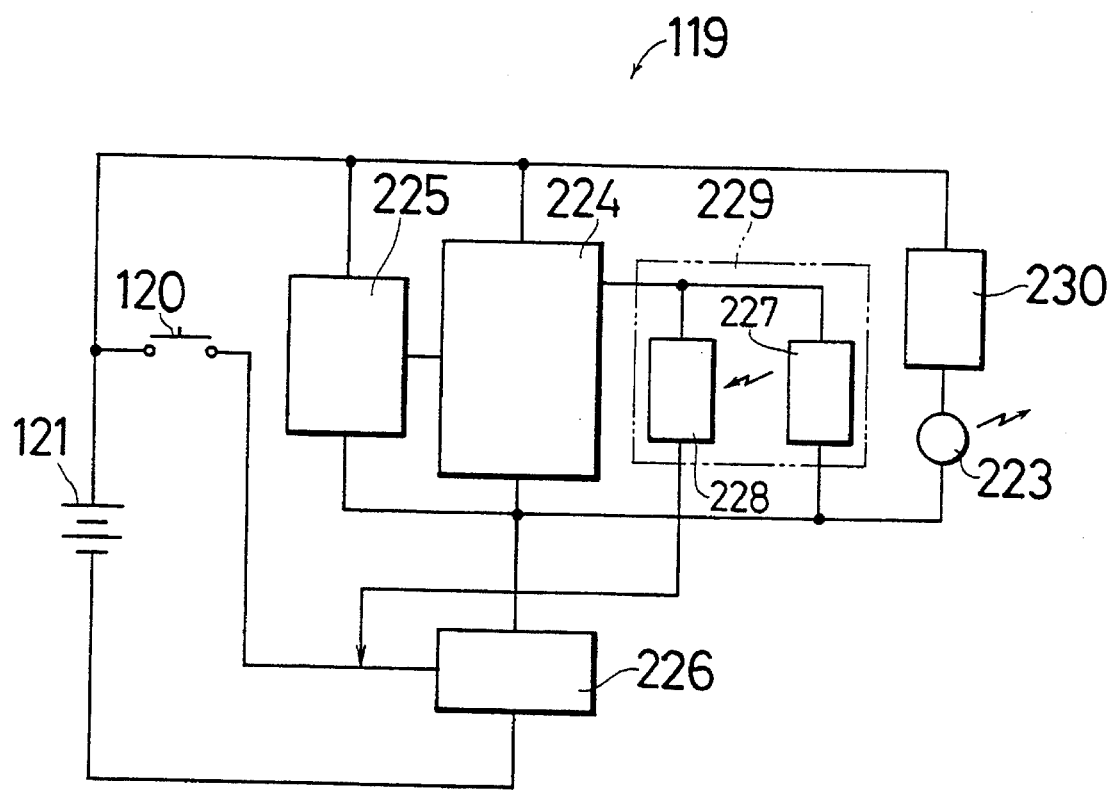
FIG. 20 is a block diagram showing an embodiment of a light source control circuit according to the invention.

FIG. 20 is a block diagram showing an embodiment of a light source circuit according to the invention. A light source control circuit 119 comprises: a timer circuit 224 for generating pulses of a specific time width, for example, 10 seconds after start of energization; an automatic trigger circuit 225 for starting the timer circuit 224; a switching element 226 for controlling the energization of the timer circuit 224 and light source 223; a conduction holding circuit 229 for insuring the conduction of the switching element 226 in response to the output of the timer circuit 224, a switch 120 for starting the switching element 226; and a battery 121 as the power source of the circuit. The conduction holding circuit 229 and switching element 226 compose a switching circuit for energizing the light source 223 while the timer circuit 224 is generating pulses, and for stopping the energization of the light source 223 and timer circuit 224 when the pulse output of the timer circuit 224 is over.

The conduction holding circuit 229 is composed of a primary circuit 227 and a secondary circuit 228. The primary circuit 227 actuates the secondary circuit 228 in response to the pulse output of the timer circuit 224, and the secondary circuit 228 actuates the switching circuit 226 to effects the conduction. The switch 120 is composed of an automatic reset type push-button switch or the like. The light source 223 is selected from LED, LD, incandescent light and the like, and emits, for example, visible light. From the viewpoint of saving power consumption and reducing size, LED is preferred as the light source 223. A constant current circuit 230 is connected in series to the light source 223, stabilizing the light quality.

The operation is described below. When the switch 120 is made conductive temporarily by being pressed by the radiologist, a predetermined voltage is fed into the switching element 226 through the switch 120 from a cathode of the battery 121, and the switching element 226 is set in a conductive state. As a result, a supply voltage of the battery 121 is applied to the automatic trigger circuit 225, timer circuit 224, light source 223, etc. connected in series to the switching element 226. The timer circuit 224 delivers a high level power immediately after start of energization by the automatic trigger circuit 225, and drives the primary circuit 227. The primary circuit 227 then drives the secondary circuit 228 through information medium such as light. When the secondary circuit 228 becomes a conductive state, a predetermined voltage is applied to the switching element 226 to be in a conductive state. Once the secondary circuit 228 is made conductive in this way, the switching element 226 is kept in a conductive state, and the light source 223 is energized to emit light, even if the switch 120 is later reset automatically to open.

On the other hand, after lapse of specified time from start of energization, the output of the timer circuit 224 is inverted to a low level. Consequently, the primary circuit 227 is stopped, and the secondary circuit 228 is made cut-off state, and voltage is no longer applied to the switching element 226. Then, the switching element 226 is cut off. The energization to the light source 223 is stopped, so is energization to the automatic trigger circuit 225 and timer circuit 224 Thus, for a specific time after actuation of the switch 120, the light source 223 keeps emitting light, and when the light source 223 goes out, the energization of the timer circuit 224 stops so that wasteful power consumption can be prevented.

Figure 21:
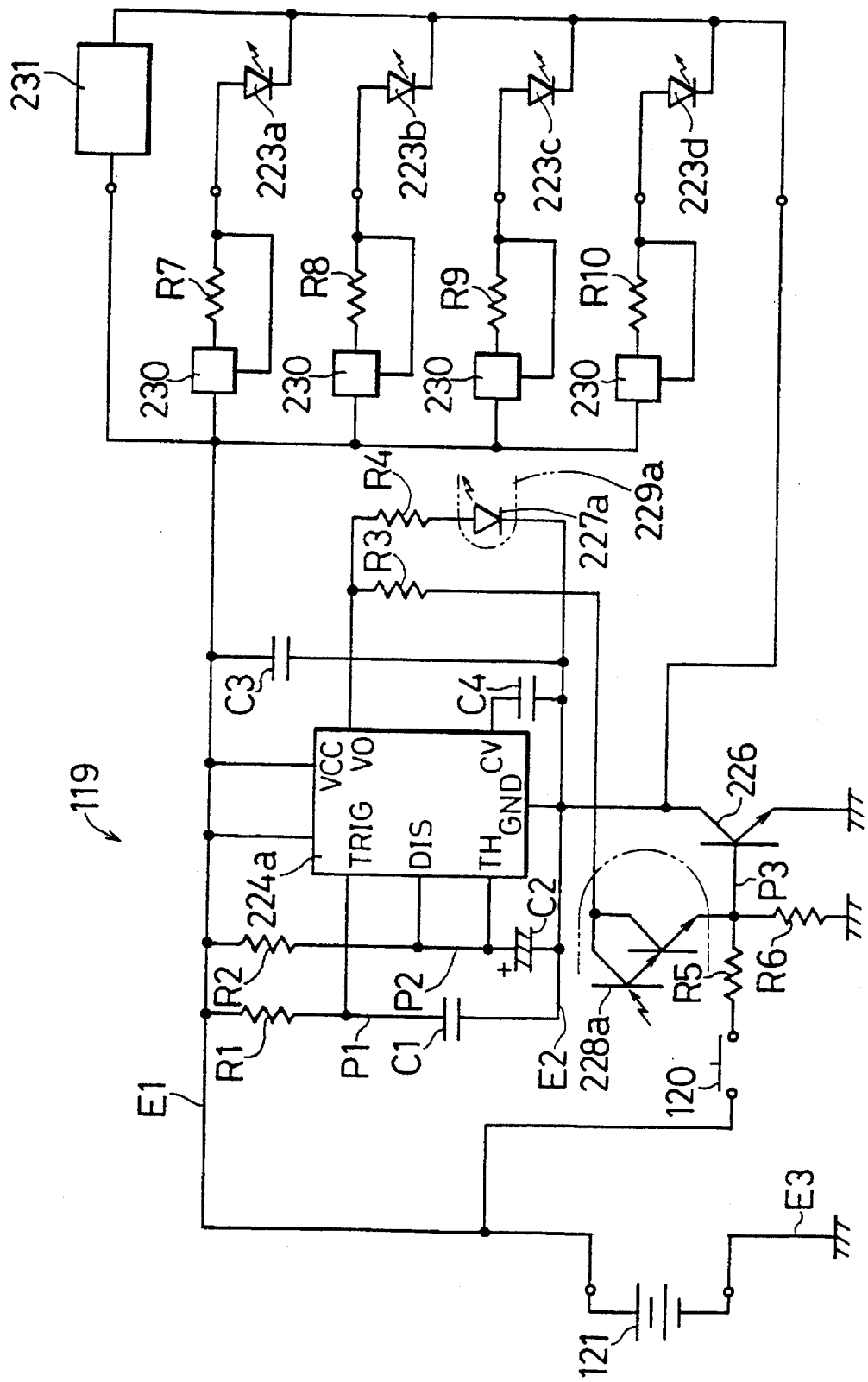
FIG. 21 is a diagram showing an actual circuit example of the light source control circuit shown in FIG. 20.

FIG. 21 is a circuit example of the light source control circuit 119 shown in FIG. 20. A timer IC (integrated circuit) 224a comprises two comparators, an RS flip-flop operated by their outputs, and a reference voltage unit that supplies reference voltages of ⅓ and ⅔ of the power source (e.g., battery) voltage to the comparator. For example, an IC of low power consumption CMOS type referred to as 555 (model μ PD555C of Nippon Electric Co.) is used as the timer IC. The automatic trigger circuit 225 is composed of a resistance R1 and a capacitor C1 connected in series between line E1 (connected to the cathode of the battery 121) and line E2 at a intermediate potential, and this connection wire P1 is connected to terminal TRIG of the timer IC 224a. Further between the line E1 and line E2, a resistance R2 and a capacitor C2 are connected in series, and this connection wire P2 is connected to terminal DIS and terminal TH of the timer IC 224a. Terminal VCC of the timer IC 224a is connected to the line E1, and terminal GND is connected to the line E2. Between the line E1 and line E2, a capacitor C3 is connected, and a capacitor C4 is connected between a terminal CV and the line E2. Between a terminal VO which is the output terminal of the timer IC 224a and the line E2, an LED 227a that comprises a photo coupler 229a is connected through a resistance R4. Between the terminal VO and a connection wire P3, a photo transistor 228a that comprises the photo coupler 229a is connected through the resistance R3. Instead of the photo coupler 229a, a high insulation switch such as relay and transformer can be used, but the photo coupler is preferred from the viewpoint of power saving and compactness.

On the other hand, the switch 120 is connected between the line E1 and the connection wire connected through a resistance R5. A resistance R6 is connected between the E3 connected to the anode of the battery 121 and the connection wire P3. Between the line E1 and line E2, a switching element 226 such as bipolar transistor and FET (field effect transistor) is connected, and its input side is connected to the connection wire P3. As the switching element 226, the bipolar transistor is preferred because the voltage drop is smaller and resistance to noise is excellent.

Further between the line E1 and line E2, a constant current circuit 230, a resistance R7, and a light source 223a are connected in series, and similarly, the constant current circuit 230, a resistance R8 and a light source 223b are connected in series. The constant current circuit 230, a resistance R9 and a light source 223c are connected in series, and the constant current circuit 230, a resistance R10, a light source 223d, and a buzzer for generating a sound are connected in series. The constant current circuit 230 stabilizes current flowing into the light sources 223a to 223d, and, for example, an IC (model LM317L of National Semiconductor Co.) is used.

The operation is described below. When the switch 120 is made conductive, a current flows into the switching element 226 from the line E1 through the switch 120 and the resistance R5, and the switching element 226 is set in a conductive state. Consequently, a supply voltage is applied between the line E1 and line E2, and a negative pulse is applied to the connection wire P1 and terminal TRIG, rendering the terminal VO a high level. Next, a current flows into the LED 227a through the resistance R4, and the LED 227a emits light, and the photo transistor 228a is set in a conductive state. As a result, a current is supplied to the connection wire P3 from the terminal VO through resistance R3, and is fed into the switching element 226. Thus, even if the switch 120 is opened later, the switching element 226 is maintained in a conductive state, and the light sources 223a to 223d are energized to emit light, and the buzzer 231 is also energized to generate a sound.

On the other hand, when a supply voltage is applied between the line E1 and line E2, the potential of the connection wire P2 is raised by an exponential function according to the time constant determined by the resistance R2 and the capacitor C2. When the potential exceeds a specific threshold value after lapse of specified time from start of energization, the terminal VO of the timer IC 224a is inverted to a low level. Next, the LED 227a is turned off, and the photo transistor 228a is made a cut-off state, and the potential of the connection wire P3 reaches the same as that of the line E3, and the switching element 226 is cut off. As a result, energization to the light sources 223a to 223d discontinues, and so does the energization to the timer IC 224a. Thus, the light sources 223a to 223d are put out, and the energization of the timer IC 224a stops. Thus, unnecessary consumption of the battery 121 can be prevented.

Figure 22:
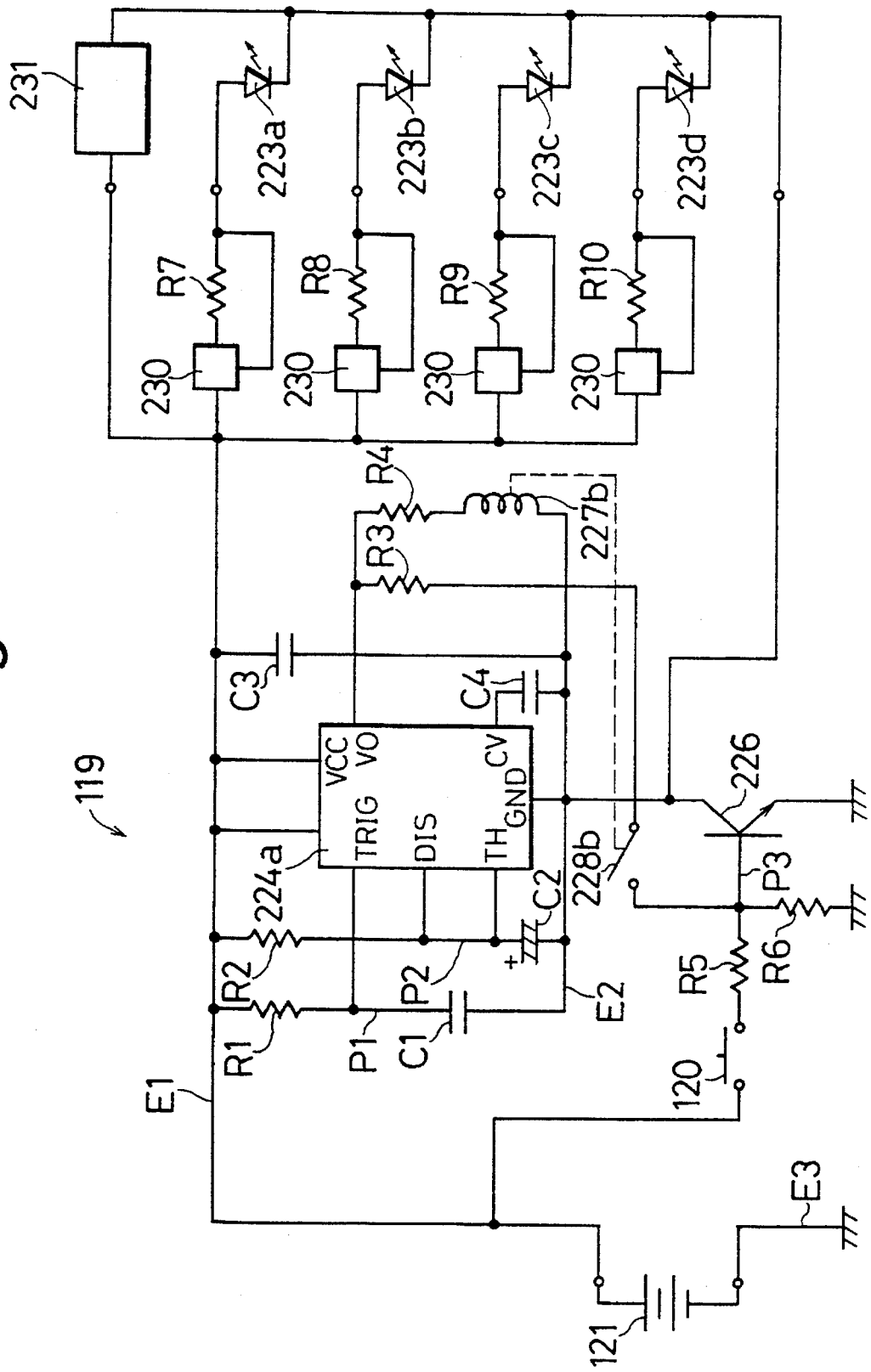
FIG. 22 is a diagram showing another circuit example of the light source control circuit shown in FIG. 20.

FIG. 22 is another circuit example of the light source control circuit 119 as shown in FIG. 20. The light source control circuit 119 in FIG. 22 is almost the same as the one shown in FIG. 21, except that a relay composed of coil 227b and a contact 228b is used instead of the photo coupler 229a.

Therefore, the same elements are identified with the same reference numbers, and repeated explanations are omitted.

The operation is described below. When the switch 120 becomes conductive, a current flows into the switching element 226 from line E1 through the switch 120 and the resistance R5, and the switching element 226 is set in a conductive state. Consequently, a supply voltage is applied between the line E1 and the line E2, and a negative pulse is applied to the connection wire P1 and the terminal TRIG rendering the terminal VO a high level. Next, a current flows into the coil 227b and the contact 228b is set in a conductive state. In turn, a current is supplied to the connection wire P3 from the terminal VO through the resistance R3, and is fed into the switching element 226. Thus, even if the switch 120 is opened later, the switching element 226 is maintained in a conductive state, and hence the light sources 223a to 223d are energized to emit light, and the buzzer 231 is also energized to sound.

On the other hand, when a supply voltage is applied between the line E1 and line E2, the potential of the connection wire F2 is raised by an exponential function according to the time constant determined by the resistance R2 and the capacitor C2. When the potential exceeds a specific threshold value after lapse of specified time from start of energization, the terminal VO of the timer IC 224a is inverted to a low level. Next, the coil 227b is turned off, and the contact 228b is set in a cut-off state, and the potential of the connection wire P3 reaches the same as that of the line E3, and the switching element 226 is cut off. As a result, energization to the light sources 223a to 223d is cut off, and the energization to the timer IC 224a is also stopped. Thus, the light sources 223a to 223d are put out, and the energization of the timer IC 224a stops. Thus, unnecessary consumption of the battery 121 can be prevented.

Figure 23:
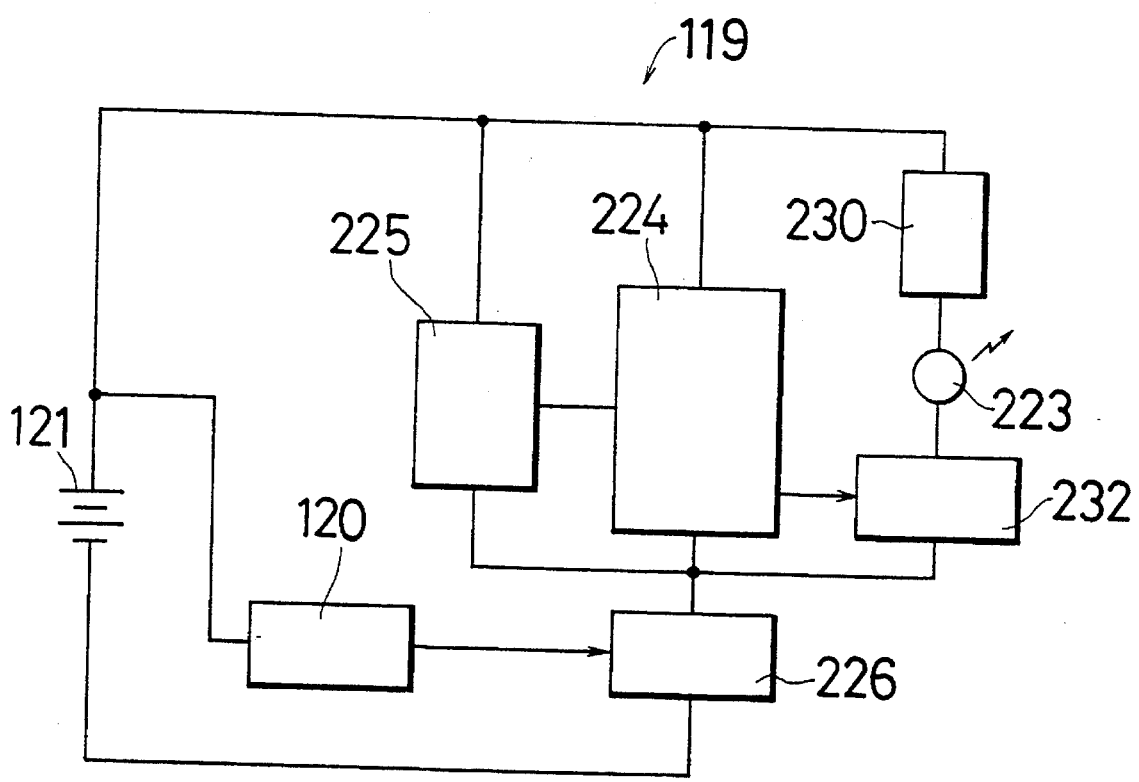
FIG. 23 is a block diagram showing a different embodiment of a light source control circuit according to the invention.

FIG. 23 is a block diagram showing a different embodiment of the light source control circuit of the invention. The light source control circuit 119 comprises a timer circuit 224 for generating pulses of specific time width of, for example, 10 seconds after start of energization, an automatic trigger circuit 225 for starting the timer circuit 224, a switching element 226 for controlling the energization of the timer circuit 224 and a light source 223, a switching element 232 for controlling the energization of the light source 223 in response to the output of the timer circuit 224, a switch 120 for actuating the switching element 226, and a battery 121 as the power source of the circuit. As the switching element 226, a thyristor is used preferably from the viewpoint of a smaller size and a longer life. The thyristor has the ability to hold the conductive state while a current is flowing into the light source 223, and to be set in a cut-off state while current is not flowing into the light source 223. The switching elements 226, 232 forms a switching circuit for energizing the light source 223 while the timer circuit 224 is generating pulses, and for stopping the energization of the light source 223 and timer circuit 224 when the pulse output of the timer circuit 224 discontinues.

The switch 120 is composed of an automatic reset type pushbutton switch or the like. The light source 223 is selected from LED, LD, incandescent lamp, or the like, and emits, for example, visible light. As the light source 223, the LED is desired from the viewpoints of power consumption, price, safety and compactness. A constant current circuit 230 is connected in series to the light source 223, and stabilizes the quantity of light.

The operation is described below. When the switch 120 conducts temporarily by being pressed by the radiologist, a predetermined voltage is fed into the switching element 226 through the switch 120 from the cathode of the battery 121, and the switching element 226 is set in a conductive state. As a result, a supply voltage of the battery 121 is applied to the automatic trigger circuit 225, time circuit 224, light source 223, etc. connected in series to the switching element 226. The timer circuit 224 delivers a high level output immediately after start of energization by the automatic trigger circuit 225, and drives the switching element 232 to be conductive state. Then a large current flows into the light source 223, and even if the switch 120 is later reset automatically to open, the switching element 226 is maintained in a conductive state, and the light emission of the light source 223 continues.

On the other hand, after lapse of specified time from start of energization, the output of the timer circuit 224 is inverted to a low level. Consequently, the switching element 232 is cut off, and the energization of the light source 223 stops, and the current flowing into the switching element 226 becomes less than the holding current to be set in a cut-off state. Thus, for a specific time after actuation of the switch 221, the light source 223 keeps emitting light, and when the light source 223 goes out, the energization of the timer circuit 224 stops so that wasteful power consumption can be prevented.

Figure 24:
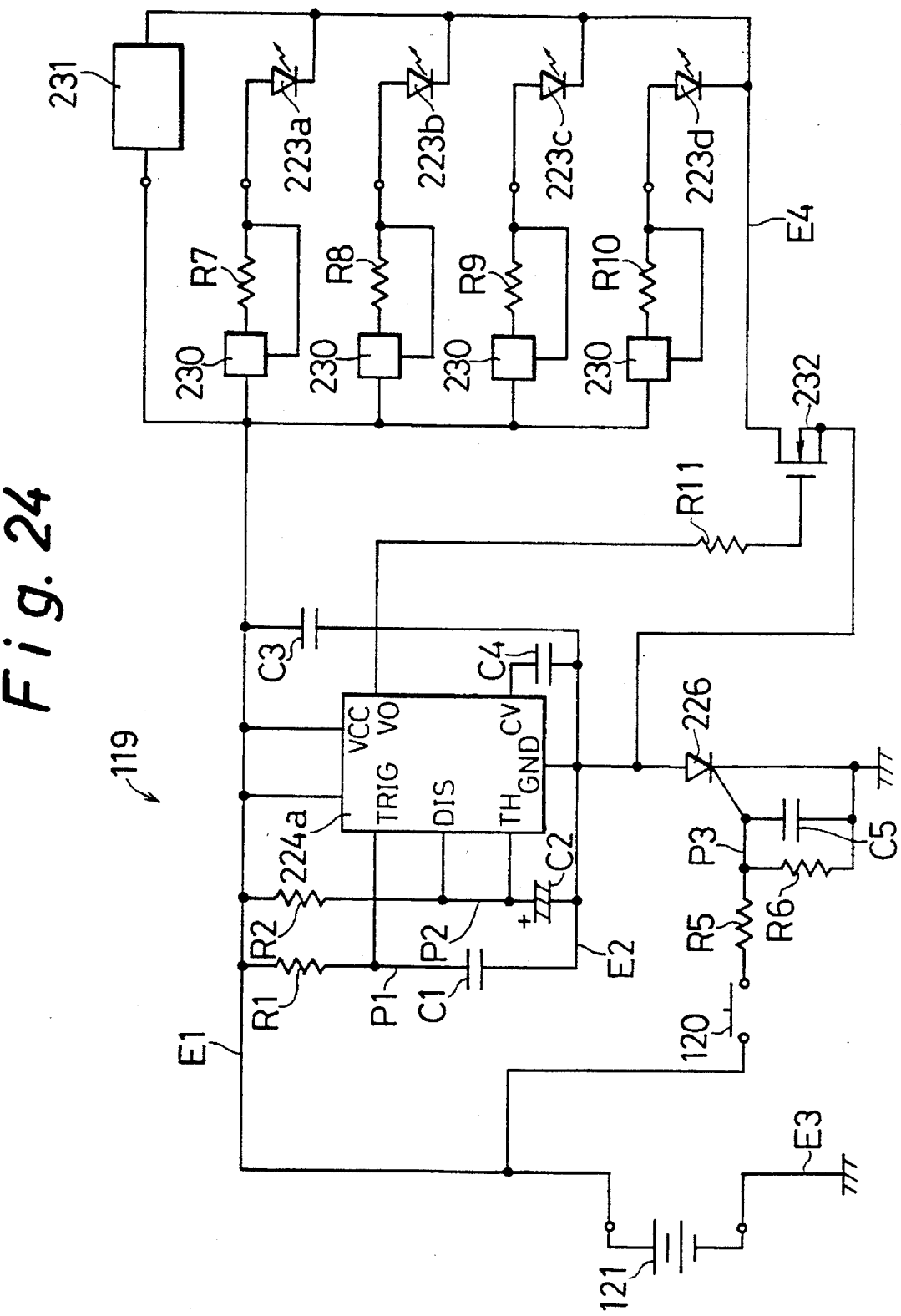
FIG. 24 is a diagram showing an actual example of the light source control circuit shown in FIG. 23.

FIG. 24 is a circuit example of the light source control circuit 119 shown in FIG. 23. A timer IC (integrated circuit) 224a comprises two comparators, an RS flip-flop operated by their outputs, and a reference voltage unit for supplying reference voltages of ⅓ and ⅔ of the supply voltage to the comparators. For example, an IC of low power consumption CMOS type referred to as 555 (model μ PD555C of Nippon Electric Co.) is used as the timer IC. An automatic trigger circuit 225 is composed of a resistance R1 and a capacitor C1 connected in series between a line E1 connected to the cathode of the battery 121 and a line E2 at intermediate potential, and this connection wire P1 is connected to a terminal TRIG of the timer IC 224a. Further between the line E1 and line E2, a resistance R2 and a capacitor C2 are connected in series, and this connection wire P2 is connected to a terminal DIS and a terminal TH of the timer IC 224a. The timer time is determined by the time constant of the resistance R2 and capacitor C2. Terminal VCC of the timer IC 224a is connected to the line E1, and a terminal GND is connected to the line E2. Between the line E1 and line E2, a capacitor C3 is connected, and a capacitor C4 is connected between the terminal CV and the line E2. Terminal VO, which is the output terminal of the timer IC 224a, is connected to the input of the switching element 232 such as FET through a resistance R11.

On the other hand, between the line E1 and connection wire P3, the switch 120 is connected through a resistance R5. A resistance R6 and a capacitor C5 are connected between the line E3 (connected to the anode of the battery 121) and the connection wire P3. Between the line E3 and the line E2, a switching element 226 such as a thyristor is connected, and the input of the switch is connected to the connection wire P3.

Further, between the line E2 and the line E4, a switching element 232 is connected, and between the line E4 and the line E1, a constant current circuit 230, a resistance R7, and a light source 223a are connected in series. Similarly, the constant current circuit 230, a resistance R8 and a light source 223b are connected in series; the constant current circuit 230, a resistance R9 and a light source 223c are connected in series; and the constant current circuit 230, a resistance R10 and a light source 223d are connected in series, and to which a buzzer 231 for generating a sound is connected. The constant current circuit 230 stabilizes the current flowing into the light sources 223a to 223d, and, for example, an IC (model LM317L of National Semiconductor Co.) is used as the constant current circuit.

The operation is described below. When the switch 120 is made conductive, a Predetermined voltage is fed into the switching element 226 from the line E1 through the switch 120 and resistance R5, and the switching element 226 is set in a conductive slate. Consequently, a supply voltage is applied between the line E1 and the line E2, and the potential of the connection wire P1 and the terminal TRIG rises sharply, and the terminal VO becomes a high level. Next, a voltage is fed into the switching element 232 through the resistance R11, and the switching element 232 is set in a conductive state. Next, a large current flows into the light sources 223a to 223d to emit light, and the buzzer 231 is also energized to generate a sound. Thus, even if the switch 221 is later opened, as far as the large current is flowing into the switching element 226, the switching element 226 is maintained in a conductive state. The current flowing in the switching element 226 is about 130 mA, which exceeds the self-holding current of Ith=3 mA of the switching element 225.

On the other hand, when a supply voltage is applied between the line E1 and line E2, the potential of the connection wire P2 is raised by an exponential function according to the time constant determined by the resistance R2 and the capacitor C2. When the potential exceeds a specific threshold value after lapse of specified time from start of energization, the terminal VO of the timer IC 224a is inverted to a low level. Next, the switching element 232 is turned off, and the energization to the light sources 223a to 223d is cut off, and the current flowing into the switching element 226 becomes a small current of the timer IC 224a or the like, for example, about 0.8 mA. As a result,the switching element 226 cannot maintain conduction, and the energization to the timer IC 224a is also discontinued. Thus, the light sources 223a to 223d are put out, and the energization of the timer IC 224a stops so that unnecessary consumption of the battery 121 can be prevented.

Figure 25:
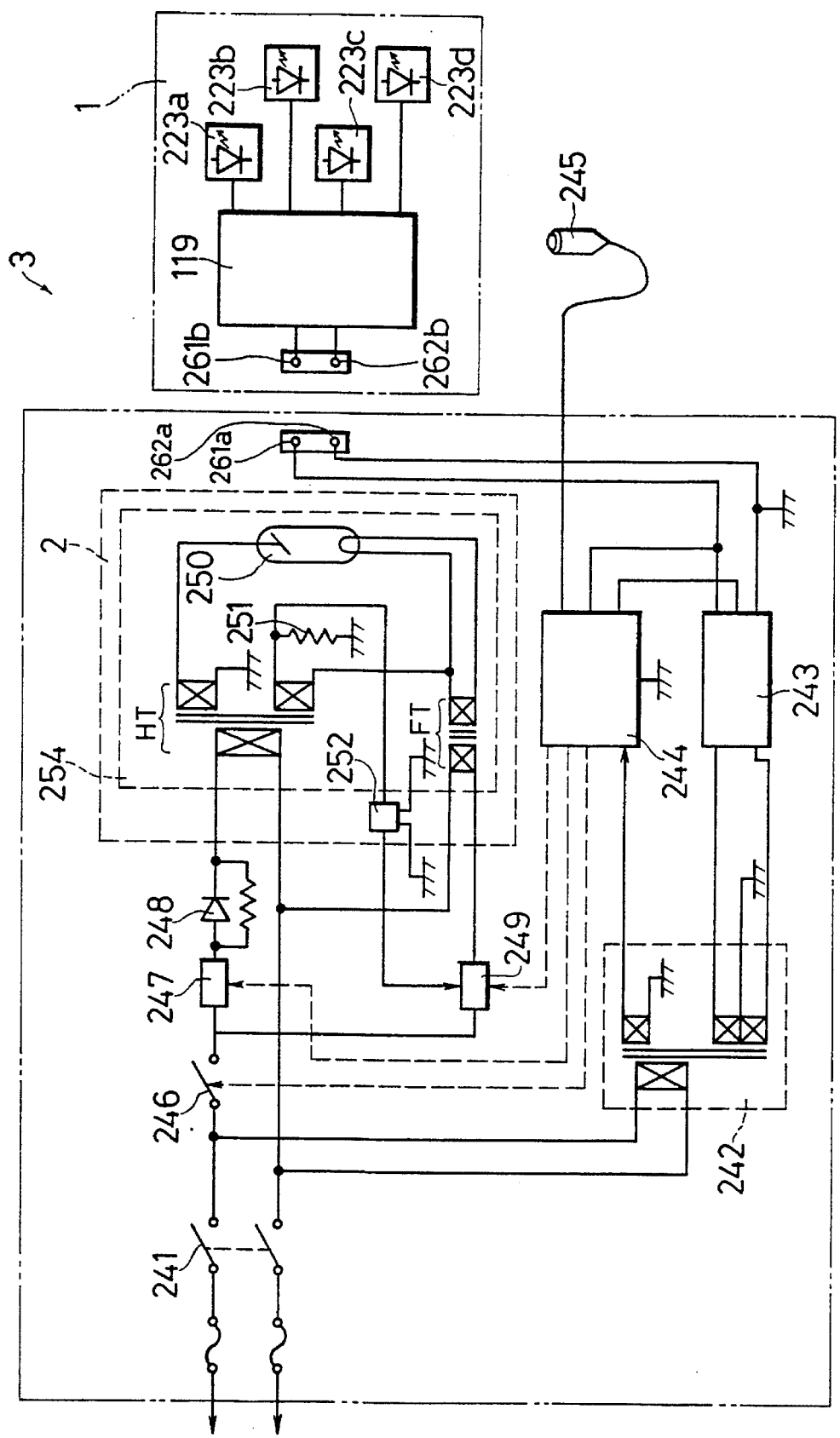
FIG. 25 is a block diagram of an electrical circuit included in the medical X-ray apparatus shown in FIG. 3.

FIG. 25 is a block diagram showing an electric constitution of the medical X-ray apparatus shown in FIG. 3. The medical X-ray apparatus 3 comprises an X-ray generation unit 2 for generating X-ray, an irradiation tube 1 detachably fitted to the X-ray irradiation port of the X-ray generation unit 2 for emitting a cross slit light as shown in FIG. 8, an X-ray control circuit 244 for controlling the X-ray generation unit 2, and a power source circuit 243 for feeding electric power to the X-ray control circuit 244.

The X-ray generation unit 2 comprises a high voltage transformer HT for generating a high voltage from a commercial power source of AC 100 V or the like, an X-ray tube 250 for generating an X-ray when a high voltage is applied from the secondary side of the high voltage transformer HT, a low voltage transformer FT for igniting the filament of the X-ray tube 250, a load resistance 251 of the X-ray tube 250, and a filament current adjusting circuit 252 for adjusting the filament current 252. In order to enhance electric insulation, components other than the filament current adjusting circuit 252 are immersed in an oil tank 254.

The commercial power source is connected to the X-ray apparatus 3 through a fuse and a power switch 241, and is connected to the X-ray generation unit 2 through a backup relay 246, and is further connected to the primary side of the high voltage transformer HT through an AC switch 247 such as triac, and a counter voltage preventive circuit 248 such as diode, and is also connected to the primary side of the low voltage transformer FT through an AC switch 249 such as triac. The commercial power source is connected to the primary side of the control transformer 242, and to its secondary side, the X-ray control circuit 244 and power source circuit 243 are connected. The power source circuit 243 rectifies AC and delivers a stabilized DC voltage to the X-ray control circuit 244, as well as to connection electrodes 261a, 262a electrically connected to connection electrodes 261b, 262b of the irradiation tube 1.

The light source control circuit 119 is mounted in the irradiation tube 1 as shown in FIG. 22 to FIG. 24, and the power source is supplied from the power source circuit 243 through the connection electrodes 261b, 262b, instead of the built-in battery 121.

The operating procedure of X-ray generation is briefly described below. When the radiologist presses an exposure button 245 connected to the X-ray control circuit 244, the backup relay 246 conducts, and the AC switch 249 also conducts, and then a current flow into the low voltage transformer FT, thereby lighting the filament of the X-ray tube 250. About two seconds later, the filament is sufficiently heated, and the AC switch 247 conducts and a current flow into the high voltage transformer HT, and a high voltage is applied to the X-ray tube 240 for a specific time, thereby emitting X-ray during this period. At the same time, a voltage corresponding to the high voltage current is generated at both ends of the load resistance 251, and it is monitored by the filament current adjusting circuit 252. If the high voltage current increases, the filament current adjusting circuit 252 controls the current quantity of the AC switch 249 thereby to decrease the filament current. The X-ray irradiation quantity of the X-ray tube 250 may be finally stabilized. After lapse of specific time from start of high Voltage application, the AC switch 247 is disconnected, and X-ray generation discontinues. Slightly later, the backup relay 246 is cut off, and therefore, the high voltage can be securely cut off, in case the AC switch 247 is defective.

Figure 26:
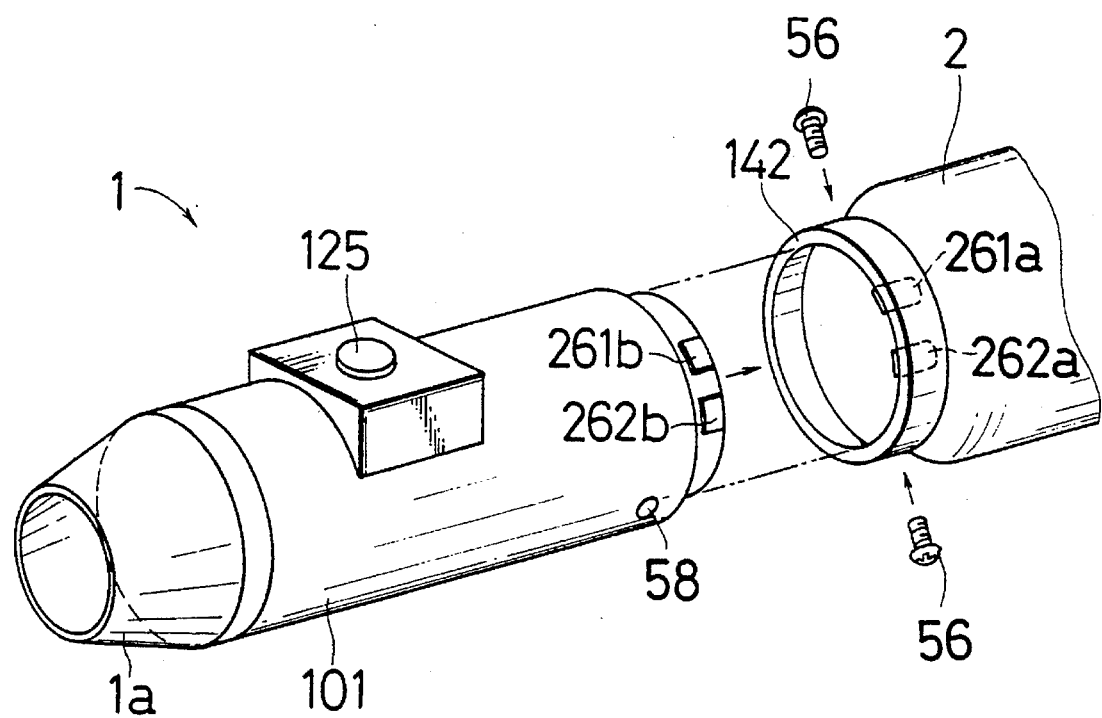
FIG. 26 is a partial perspective view showing the manner in which an irradiation tube is installed in an X-ray radiation port of the X-ray generation unit in the practice of the invention.

FIG. 26 is a partial perspective view showing a mode in which the irradiation tube 1 is mounted on the housing end 55 of the X-ray generation unit 2. The connection electrodes 261b, 262b are provided at the mounting end of the tube body 101, and when mounted on the end 55 of the X-ray generation unit 2, the connection electrodes 261a, 262a and the connection electrodes 261b, 262b are electrically connected with each other. Furthermore, through a mounting hole 58 drilled in the tube body 101 (by tightening the screw 56 into the X-ray irradiation port 142) the irradiation tube 1 is fixed to the X-ray generation unit 2.

In the embodiment, it is not necessary to install a power source in the irradiation tube 1 itself, and further reduction of size and weight may be possible. Moreover, since a stable voltage is supplied to the tube from the power source circuit 243, a stable quantity of light is obtained. Therefore, the constant current circuit 230 for stabilizing the power source can be omitted.

The invention may be practiced in indicating the emitting position of not only X-ray, but also of other invisible electromagnetic waves, such as infrared ray, ultraviolet ray and laser light, and therefore the invention may be applied to dental field, as well as to other medical fields.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A medical X-ray apparatus comprising:

an X-ray generating unit;

an irradiation tube, formed of a light-permeable material, for defining an X-ray radiation cone from the X-ray generating unit, the irradiation tube mounted on the X-ray generating unit so as to angularly displace around the axis of the X-ray with respect to the X-ray generating unit and the irradiation tube having therein visible optical means disposed at intervals in the peripheral direction thereof and outside of the radiation cone, the visible optical means emitting visible light of a fan beam shape to an X-ray exposure subject to indicate an X-ray irradiation position on the X-ray exposure subject and comprising four light sources symmetrically disposed with respect to the X-ray irradiation axis, each formed of a light-emitting diode, and focusing means, formed of lenses, the focusing means focusing the light from each light source to cross the axis of the X-ray orthogonally and to form a cross slit image on the focusing plane, wherein at least one of the irradiation tube and the X-ray generation unit has a flat switch disposed on the outer circumference thereof to control on/off of the visible optical means, and when the flat switch is turned on, the light sources are lit up for a predetermined period.

2. An apparatus according to claim 1, wherein said irradiation tube comprises:

a tube body for guiding an X-ray irradiation cone, the tube body including a base end, a tip of the base end facing an exposure subject; and a tube tip portion detachably mounted on the tube body at the base end; and said apparatus further comprises:

a support piece fixed on the tube body, the support piece projecting forward from the base end and supporting the tube tip portion at the tip of the base end, wherein the length of the support piece being projected is selected to be a value that insures a permissible distance SSD between a focus of the X-ray and an irradiation surface of the exposure subject.

3. The medical X-ray apparatus of claim 1, wherein a tip of the irradiation tube is detachable from the irradiation tube.

4. The irradiation tube of claim 1, wherein the tube body has a battery built therein for feeding electric power to the visible optical means.

* * * * *